(12) United States Patent
Hamamatsu et al.

(10) Patent No.: US 8,654,350 B2
(45) Date of Patent: Feb. 18, 2014

(54) INSPECTING METHOD AND INSPECTING APPARATUS FOR SUBSTRATE SURFACE

(71) Applicants: Akira Hamamatsu, Chiba (JP); Yoshimasa Oshima, Yokohama (JP); Shunji Maeda, Yokohama (JP); Hisae Shibuya, Chigasaki (JP); Yuta Urano, Yokohama (JP); Toshiyuki Nakao, Yokohama (JP); Shigenobu Maruyama, Oiso (JP)

(72) Inventors: Akira Hamamatsu, Chiba (JP); Yoshimasa Oshima, Yokohama (JP); Shunji Maeda, Yokohama (JP); Hisae Shibuya, Chigasaki (JP); Yuta Urano, Yokohama (JP); Toshiyuki Nakao, Yokohama (JP); Shigenobu Maruyama, Oiso (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/672,742

(22) Filed: Nov. 9, 2012

(65) Prior Publication Data

US 2013/0107247 A1  May 2, 2013

Related U.S. Application Data

(63) Continuation of application No. 13/404,749, filed on Feb. 24, 2012, now Pat. No. 8,310,665, which is a continuation of application No. 12/470,505, filed on May 22, 2009, now Pat. No. 8,144,337.

(30) Foreign Application Priority Data

May 23, 2008 (JP) .................. 2008-134945
Oct. 10, 2008 (JP) .................. 2008-263397

(51) Int. Cl.
*G01B 11/30* (2006.01)

(52) U.S. Cl.
USPC ........................ 356/600; 356/237.4

(58) Field of Classification Search
USPC ................ 356/600, 445–448, 237.1–237.5
See application file for complete search history.

(56) References Cited

U.S. PATENT DOCUMENTS

| 4,290,698 | A | * | 9/1981 | Milana .......................... 356/600 |
| 5,352,038 | A | * | 10/1994 | Schmidt et al. .................. 374/45 |
| 6,989,548 | B2 | * | 1/2006 | Tange et al. ............. 250/559.45 |
| 7,002,689 | B2 | * | 2/2006 | Liu et al. ........................ 356/432 |
| 7,362,425 | B2 | * | 4/2008 | Meeks et al. ..................... 356/73 |
| 7,764,367 | B2 | | 7/2010 | Matsui |
| 8,144,337 | B2 | | 3/2012 | Hamamatsu et al. |

(Continued)

FOREIGN PATENT DOCUMENTS

JP   2003-130808   5/2003

OTHER PUBLICATIONS

"Calculation of the Power Spectral Density From Surface Profile Data", Elson et al, Jan. 1, 1995, vol. 34, No. 1., Applied Optics 1995 Optical Society of America.

(Continued)

*Primary Examiner* — Hoa Pham
(74) *Attorney, Agent, or Firm* — Antonelli, Terry, Stout & Kraus, LLP.

(57) ABSTRACT

An inspecting method and apparatus for inspecting a substrate surface includes illuminating a light to the substrate surface having a film, detection of a scattered light or reflected light from a plurality of positions of the substrate surface to obtain a plurality of electrical signals, comparison of the plurality of electrical signals and a database which indicates a relationship between the electrical signals and surface roughness, and calculation of a surface roughness value based on the result of comparison.

10 Claims, 20 Drawing Sheets

(56) References Cited

U.S. PATENT DOCUMENTS

| | | |
|---|---|---|
| 2005/0094136 A1* | 5/2005 | Xu et al. ............... 356/237.3 |
| 2008/0013084 A1 | 1/2008 | Matsui et al. |
| 2008/0068593 A1* | 3/2008 | Nakano et al. ............ 356/73 |
| 2008/0174764 A1* | 7/2008 | Matsui ..................... 356/73 |
| 2009/0299655 A1 | 12/2009 | Biellak et al. |
| 2010/0265518 A1 | 10/2010 | Bills et al. |
| 2010/0271625 A1* | 10/2010 | Matsui ................ 356/237.3 |

OTHER PUBLICATIONS

"Light Scattering by a Sphere on a Substrate", Bobbert et al, Physica 137A (1986) 209-242, North-Holland, Amsterdam.

"Reflection of Electromagnetic Waves From Slightly Rough Surfaces", Rice et al, Bell Telephone Laboratories, pp. 351-378, Jun. 1950 Symposium on Theory of Electromagnetic Waves, Sponsorship of Washington Square College of Arts and Science.

"Light Scattering From Surfaces With a Single Dielectric Overlayer", Elson, J. Opt. Soc. Am., vol. 66, No. 7 Jul. 1976, pp. 682-694.

"Infrared Light Scattering From Surfaces Covered With Multiple Dielectric Overlayers", Elson, Applied Optics, vol. 16, No. 11, Nov. 1977, pp. 2872-2881.

"Multilayer-Coated Optics: Guided-Wave Coupling and Scattering by Means of Interface Random Roughness", Elson, 199 Optical Society of America, vol. 12, No. 4, Apr. 1995, pp. 729-742.

* cited by examiner

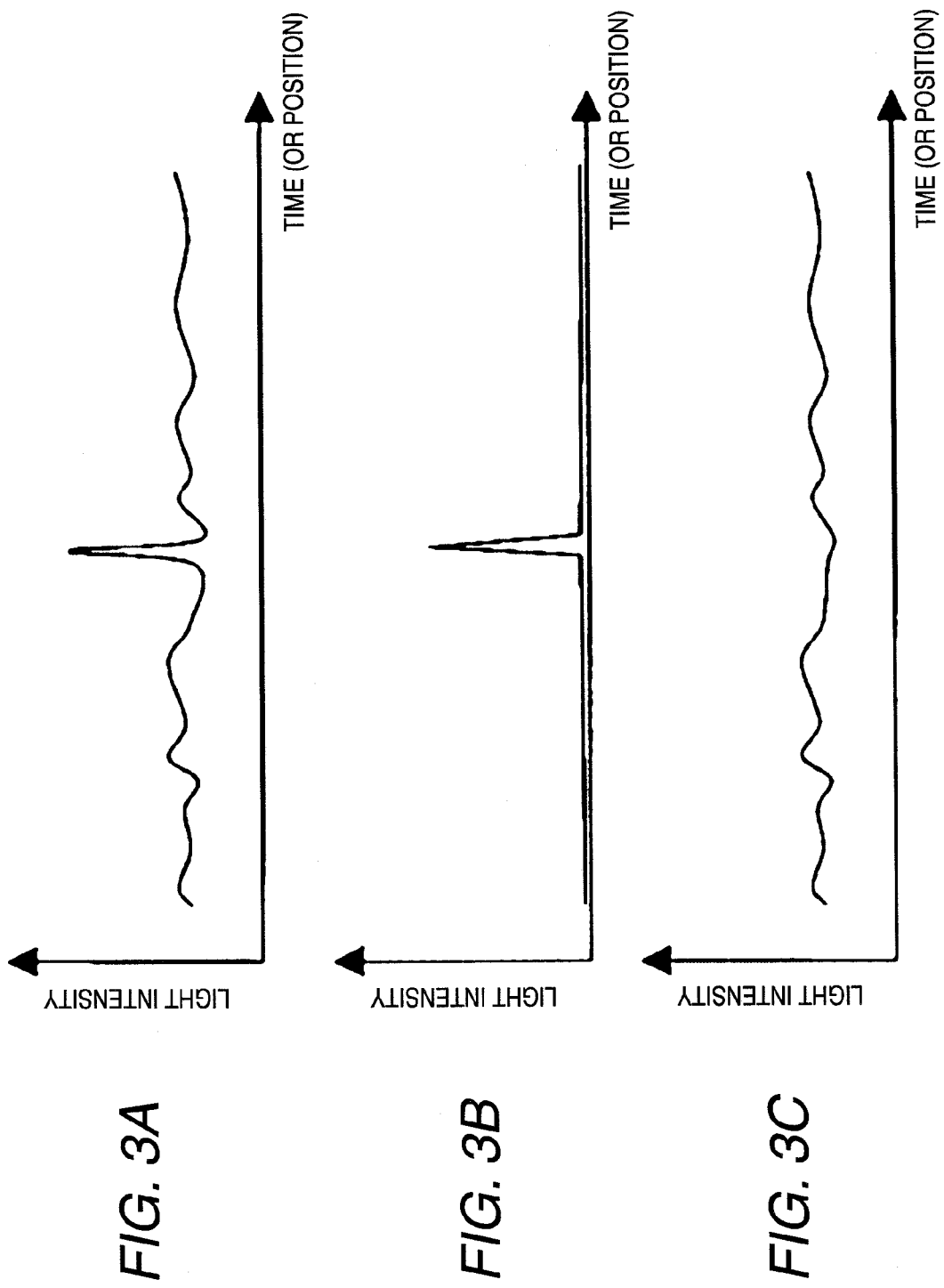

FIG. 17

MEASURED VALUE

| | DETECTOR 1 | DETECTOR 2 | ... | DETECTOR n |
|---|---|---|---|---|
| SURFACE ROUGHNESS X | s1 | s2 | ... | sn |

DATABASE

| | DETECTOR 1 | DETECTOR 2 | ... | DETECTOR n | RMS |
|---|---|---|---|---|---|
| SURFACE ROUGHNESS 1 | d11 | d12 | ... | d1n | |
| SURFACE ROUGHNESS 2 | d21 | d22 | ... | d2n | |
| ... | ... | ... | ... | ... | |
| SURFACE ROUGHNESS m | dm1 | dm2 | ... | dmn | |

WITH CORRELATION

WITHOUT CORRELATION

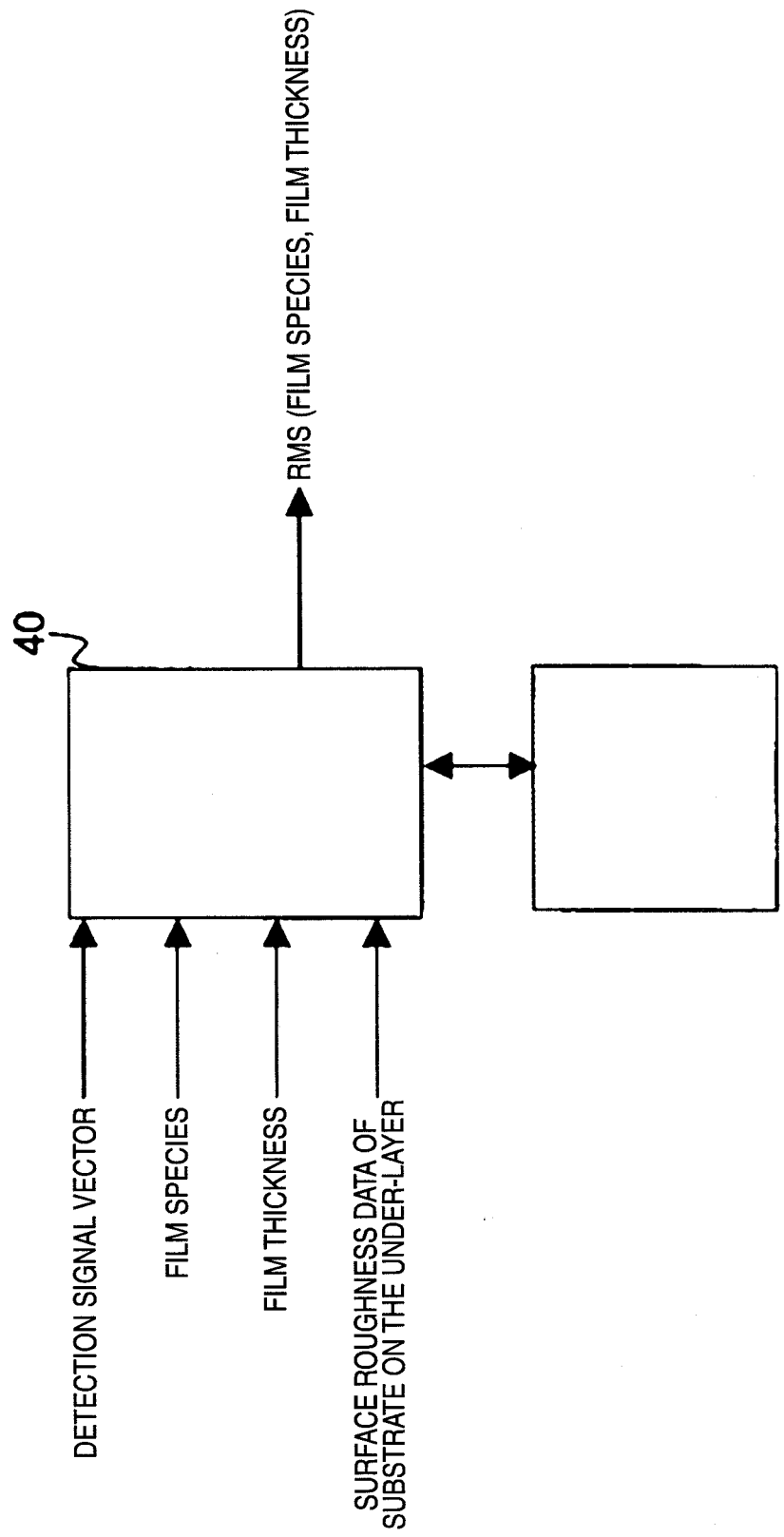

INSPECTING METHOD AND INSPECTING APPARATUS FOR SUBSTRATE SURFACE

CROSS REFERENCE TO RELATED APPLICATION

This application is a continuation of U.S. application Ser. No. 13/404,749, filed Feb. 24, 2012, which is a continuation of U.S. application Ser. No. 12/470,505, filed Feb. 22, 2009, now U.S. Pat. No. 8,144,337, the contents of which are incorporated herein by reference.

BACKGROUND OF THE INVENTION

The present invention relates to an inspecting method and an inspecting apparatus for inspecting the surface roughness existing on the surface of a substrate such as a semiconductor substrate or a hard disk substrate.

In a manufacturing line for the semiconductor substrate or thin film substrate, the inspection for defect or foreign matter existing on the surface of the semiconductor substrate or thin film substrate is made to maintain and improve the yields of products. For example, in a sample such as a semiconductor substrate before forming a circuit pattern, it is required to detect a microscopic defect or foreign matter (hereinafter called a defect) of 0.05 µm or less on the surface or microroughness (haze) on the surface. Also, to detect such defect, the conventional inspecting apparatus applies a condensed laser beam to the surface of the sample and condenses and detects a scattered light from the defect. Also, in a sample such as a semiconductor substrate after forming the circuit pattern, the sample surface is illuminated by a laser beam, a scattered light occurring on the sample surface is condensed, a diffracted light from a periodical pattern is shielded by a spatial filter, a scattered light from a non-periodic pattern and the defect is detected, and the non-periodic pattern is deleted by die comparison to recognize the defect.

A semiconductor inspection among various kinds of substrate inspection will be described below by way of example. On a wafer after passing through various kinds of semiconductor manufacturing process for a silicon wafer or film formation, there are various defects, which decrease the yields of the semiconductor products. As a degree of integration of the semiconductor product is increased, it is required that the surface inspection of the substrate has the higher sensitivity and the defects are classified and detected. There are various kinds of defects such as foreign matter, scratch and COP (crystalline defect), and further there is recently a demand for detecting the microroughness on the surface of the substrate.

These prior arts were described in patent document 1 (JP-A-2003-130808), non-patent document 1 (APPLIED OPTICS 1995 Vol. 34, No. 1 pp. 201-208), non-patent document 2 (P. A. Bobbert and J. Vlieger (Leiden Univ.): Light Scattering), non-patent document 3 (S. O. Rice, Comm. Pure and Appl. Math 4, 351 (1951)), non-patent document 4 (J. M. Elson; Light scattering from surfaces with a single dielectric overlayer; J. Opt. Soc. Am. 66, 682-694 (1976)), non-patent document 5 (J. M. Elson: Infrared light scattering from surface covered with multiple dielectric overlayers; Appl. Opt. 16, 2872-2881 (1977)), and non-patent document 6 (J. M. Elson: Multilayer-coated optics: guided-wave coupling and scattering by means of interface random roughness; J. Opt. Soc. Am. A12, 729-742 (1995)).

SUMMARY OF THE INVENTION

As the degree of integration of the semiconductor product is increased, it is required that the surface inspection of the substrate has the higher sensitivity, and the defects are classified and detected, whereby there is a demand for detecting the microroughness on the surface of the substrate as its object.

However, in the optical inspecting apparatuses as disclosed in the above documents, the inspection for the microroughness or film thickness variation existing on the substrate surface could not be made at the high sensitivity and high speed.

The invention provides an inspecting method and an inspecting apparatus for detecting the microroughness on the substrate surface at the high sensitivity and high speed.

Also, the invention provides an inspecting method and an inspecting apparatus capable of making the inspection for the microroughness and the inspection for defects on the substrate surface at the same time.

The typical inventions as disclosed in the present application will be briefly outlined as follows.

(1) An inspecting method for inspecting a substrate surface, characterized by including a first step of applying a light to the substrate surface, a second step of detecting a scattered light or reflected light from the substrate surface due to the applied light at a plurality of positions to obtain a plurality of electrical signals, a third step of extracting a signal in a mutually different frequency band from each of the plurality of electrical signals, and a fourth step of calculating a value regarding the surface roughness of the substrate surface to through an arithmetical operation process of a plurality of extracted signals in the frequency bands.

(2) The inspecting method according to (1), characterized in that the third step includes extracting the signal in the frequency band preprogrammed for each of the plurality of electrical signals.

(3) An inspecting apparatus for inspecting a substrate surface, characterized by comprising an illuminating optical system for applying a light to the substrate surface, a plurality of detecting optical systems for detecting a scattered light or reflected light from the substrate surface due to the applied light at a plurality of positions to obtain a plurality of electrical signals, and a processing section for extracting a signal in a mutually different frequency band from each of the plurality of electrical signals, and calculating a value regarding the surface roughness of the substrate surface through an arithmetical operation process of a plurality of extracted signals in the frequency bands.

(4) The inspecting apparatus according to (3), characterized in that the plurality of detecting optical systems are arranged at mutually different elevation angles.

(5) The inspecting apparatus according to (3) or (4), characterized in that at least one detecting optical system of the plurality of detecting optical systems has a beam splitter for splitting the optical path of the scattered light or reflected light and a plurality of sensors arranged on a plurality of optical paths split by the beam splitter, and an analyzer is disposed on the optical path of one sensor of the plurality of sensors.

(6) The inspecting method according to (1) or (2), characterized in that the fourth step includes calculating a plurality of values regarding the surface roughness.

(7) The inspecting apparatus according to any of (3) to (5), characterized in that a plurality of pieces of information on the surface roughness are calculated.

(8) An inspecting method for inspecting a substrate surface, characterized by including a first step of applying a light to the substrate surface, a second step of detecting a scattered light or reflected light from the substrate surface due to the applied light at a plurality of positions to obtain a plurality of electrical signals, and a third step of comparing the plurality of signals and the data having the correspondences between the surface roughness on the substrate having different surface roughness and the plurality of signals and estimating the surface roughness.

(9) An inspecting apparatus for inspecting a substrate surface, characterized by comprising an illuminating optical system for applying a light to the substrate surface, a plurality of detecting optical systems for detecting a scattered light or reflected light from the substrate surface due to the applied light at a plurality of positions to obtain a plurality of electrical signals, and a processing section for calculating a value regarding the surface roughness of the substrate surface by making a comparison process between the plurality of signals and the data having the correspondences between the surface roughness on the substrate having different surface roughness and the plurality of signals.

These and other objects, features and advantages of the invention will be apparent from the following more particular description of preferred embodiments of the invention, as illustrated in the accompanying drawings.

BRIEF DESCRIPTION OF THE DRAWINGS

FIG. 3A is a view showing a detection signal waveform.

FIG. 3B is a view showing a defective signal waveform at high frequency.

FIG. 3C is a view showing a wafer surface state signal waveform at low frequency.

FIG. 9($a$2) is a view showing the cross-sectional waveform for the surface state detection value or RMS value in a state of FIG. 9($a$1).

FIG. 9($a$3) is a view showing a frequency distribution of the surface state detection value or RMS value on the entire surface of the substrate in the state of FIG. 9($a$1).

FIG. 9($b$1) is a second view showing one example of the surface state map.

FIG. 9($b$2) is a view showing the cross-sectional waveform for the surface state detection value or RMS value in the state of FIG. 9($b$1).

FIG. 9($b$3) is a view showing the frequency distribution of the surface state detection value or RMS value on the entire surface of the substrate in the state of FIG. 9($b$1).

FIG. 9($c$1) is a third view showing one example of the surface state map.

FIG. 9($c$2) is a view showing the cross-sectional waveform for the surface state detection value or RMS value in the state of FIG. 9($c$1).

FIG. 9($c$3) is a view showing the frequency distribution of the surface state detection value or RMS value on the entire surface of the substrate in the state of FIG. 9($c$1).

FIG. 9($d$1) is a fourth view showing one example of the surface state map.

FIG. 9($d$2) is a view showing the cross-sectional waveform for the surface state detection value or RMS value in the state of FIG. 9($d$1).

FIG. 9($d$3) is a view showing the frequency distribution of the surface state detection value or RMS value on the entire surface of the substrate in the state of FIG. 9($d$1).

FIG. 17 is a view showing the measurement results and the database.

FIG. 21 is a view showing the relationship between input and output in an algorithm for estimating the surface state.

DESCRIPTION OF THE PREFERRED EMBODIMENTS

The embodiments of the present invention will be described below by exemplifying an inspecting apparatus that detects a defect on the surface of a wafer without pattern formed (bare wafer, or wafer in which bare wafer is subjected to a film formation process, a washing process, or a polishing process).

The inspecting apparatus according to the invention appropriately comprises an illuminating optical system 1001 for applying light to a substrate of inspection object, a stage scanning section 1003 for inspecting all or part of the substrate, a detecting optical system 1002 for detecting the scattered light or reflected light, a signal processing section 1004 for determining the defect or haze, and a data processing control section 50 for making the post-processing for the detected defect or haze. Each configuration will be specifically described below.

Figure 1:
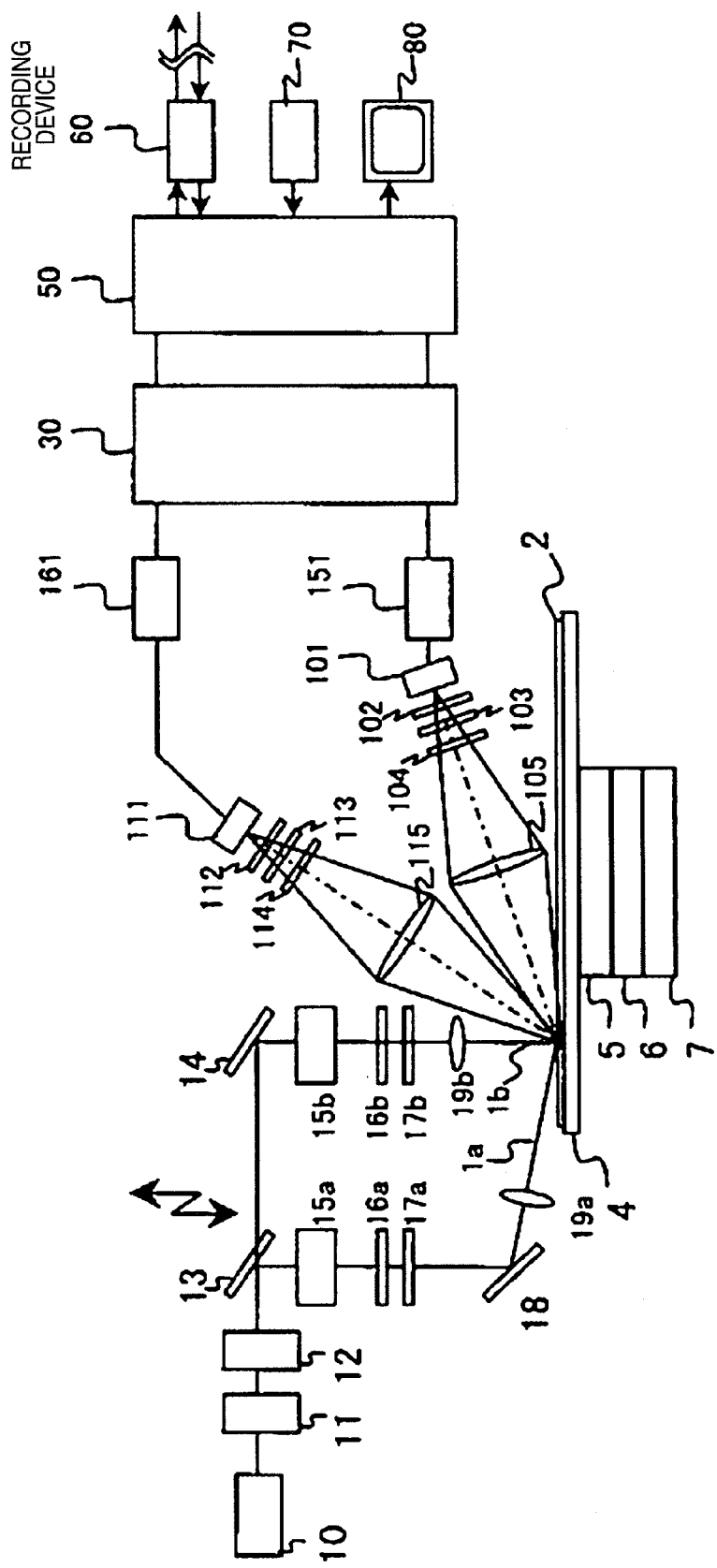
FIG. 1 is a view showing a first embodiment of an inspecting apparatus according to the present invention.

The illuminating optical system 1001 as shown in FIG. 1 has an obliquely illuminating optical system for applying an illuminating light 1a from the oblique direction to an inspection object substrate 2 and a vertically illuminating optical system for applying an illuminating light 1b from the vertical direction, which can be switched by moving a movable mirror 13, and appropriately comprises a light source 10, a light quantity adjustment mechanism 11, the light flux shape adjustment mechanisms 12, 15a and 15b, the mirrors 13, 14 and 18, the polarizers 16a and 16b, the phase shifters 17a and 17b, and the lenses 19a and 19b. The explanation is given below, taking the use of oblique illumination as an example.

A light emitted from the light source 10 such as a laser is adjusted into a desired light quantity and a beam shape through the light quantity adjustment mechanism 11 and the light flux adjustment mechanism 12, diverted in the optical path by the mirror 13 (or alternatively a beam splitter), and adjusted again in the beam shape by the light flux adjustment mechanism 15a. The light is made the specific illumination of linearly polarized light by the polarizer 16a, adjusted into a desired polarized state (P polarized light, S polarized light or C polarized light) by the phase shifter 17a, and applied via the mirror 18 and the projection lens 19a to the inspection object substrate 2. In a projected state of illumination on the inspection object substrate 2, an illumination spot 9 is linearly narrowed in an elliptical shape or in one direction, as shown in FIG. 2.

The light source 10 uses a laser of visible light wavelength band or UV wavelength band (wavelength band of 400 nm or less). Each of the light flux adjustment mechanisms 12 and 15a may be a beam expander or cylindrical lens (or alternatively an anamorphic prism), and shapes the illumination form on the substrate in combination with the projection lens 19a in the illuminating optical system 1001. The light quantity adjustment mechanism 11 is used to adjust the light quantity to desired quantity, depending on the film materials or film thickness of the substrate, using an attenuator or neutral density filter, and The polarizer 16a also functions as a wavelength selector, and is used to reduce the light other than the main wavelength component included in the illuminating light. The phase shifter 17a of a polarization adjustment section is comprised of a half-wave plate or a quarter wavelength plate, and is used to adjust polarization of illumination. In this embodiment, an optical path switching section is provided for the illumination to allow a selection between two optical paths of oblique illumination and almost vertical illumination to the substrate, but it is not required that two angles of incidence for illumination are provided, and one or three or more angles may be provided. In addition to the method for making a switching between oblique illumination and vertical illumination, using the movable mirror 13 as the optical path switching section, as shown in FIG. 1, both the oblique illumination and the vertical illumination can be effected at the same time, using a beam splitter. Though the foreign matter is typically more sensitive in the oblique illumination, a concave defect such as scratch or COP may be often more sensitive in the vertical illumination, whereby it is possible to use properly or jointly the illuminating angles depending on the defect species to be detected.

The stage scanning section 1003 is a mechanism for applying the illumination spot shaped by the illuminating optical system 1001 to all or part of the substrate surface, and comprises a substrate supporting mechanism 4 for supporting the substrate, a Z stage 5 for adjusting the height of the substrate, a θ stage 6 for rotating the substrate, and an R stage 7 for translating the substrate in the fixed direction. Herein, a scanning method for the inspection object substrate 2 will be described below using FIG. 2. If the θ stage 6 is rotated relative to the illumination spot 9 firstly applied near the edge of the inspection object substrate 2, the light is successively applied near the edge of the substrate along the circumferential direction. At the same time, if the R stage 7 is translated in one direction, the illumination spot is successively moved on the substrate surface in the circumferential direction and the radial direction, radially scanning the entire surface or any area of the substrate, as shown in FIG. 2A. Herein, if the illumination spot 9 is in the elliptical or linear form, it is possible to perform the scanning at high speed. The scanning of the illumination spot is not limited to the above method, but the specific radial position may be scanned once or multiple times, and then the R stage 7 may be moved, as shown in FIG. 2B. The focusing of the inspection object substrate 2 and the illumination spot 9 is adjusted to reach a desired height by the Z stage 5.

Figure 2C:
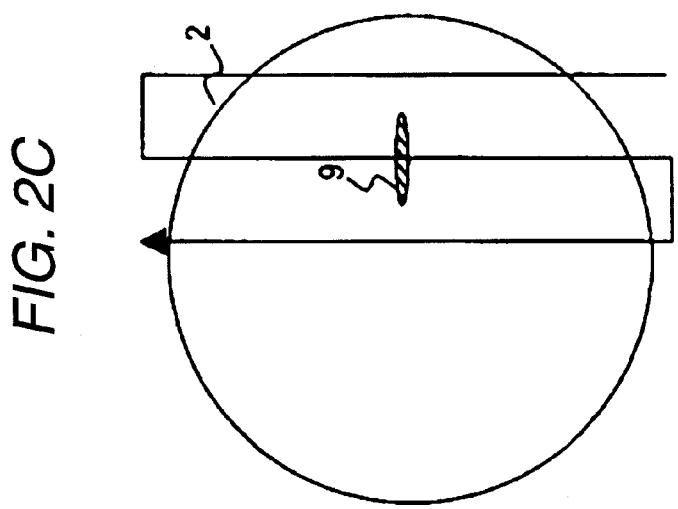
FIG. 2C is a third view showing a relatively scanning method between the substrate and the illumination.
Figure 2B:
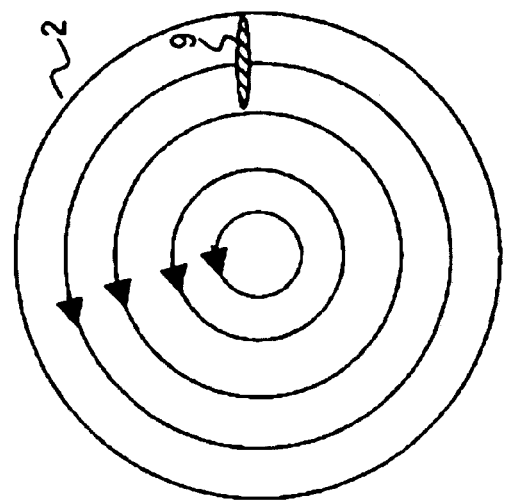
FIG. 2B is a second view showing a relatively scanning method between the substrate and the illumination.
Figure 2A:
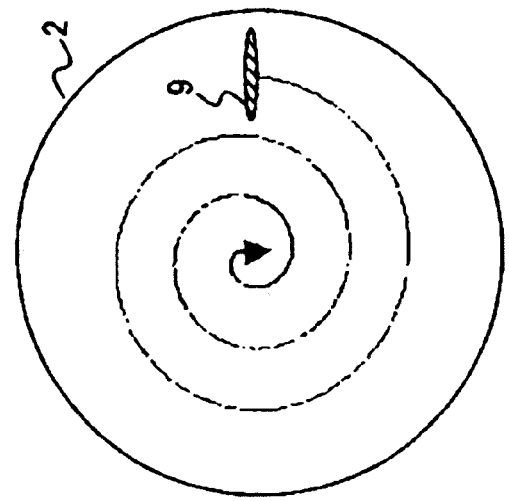
FIG. 2A is a first view showing a relatively scanning method between a substrate and an illumination.

Though the stage scanning section 1003 has been described above by exemplifying the R-θ stage, it is necessary to scan all or part of the substrate surface by the illumination spot 9 relatively moving on the substrate, in which an X-Y stage or a mechanism for moving the illumination side may be used, as shown in FIG. 2C.

Figure 4:
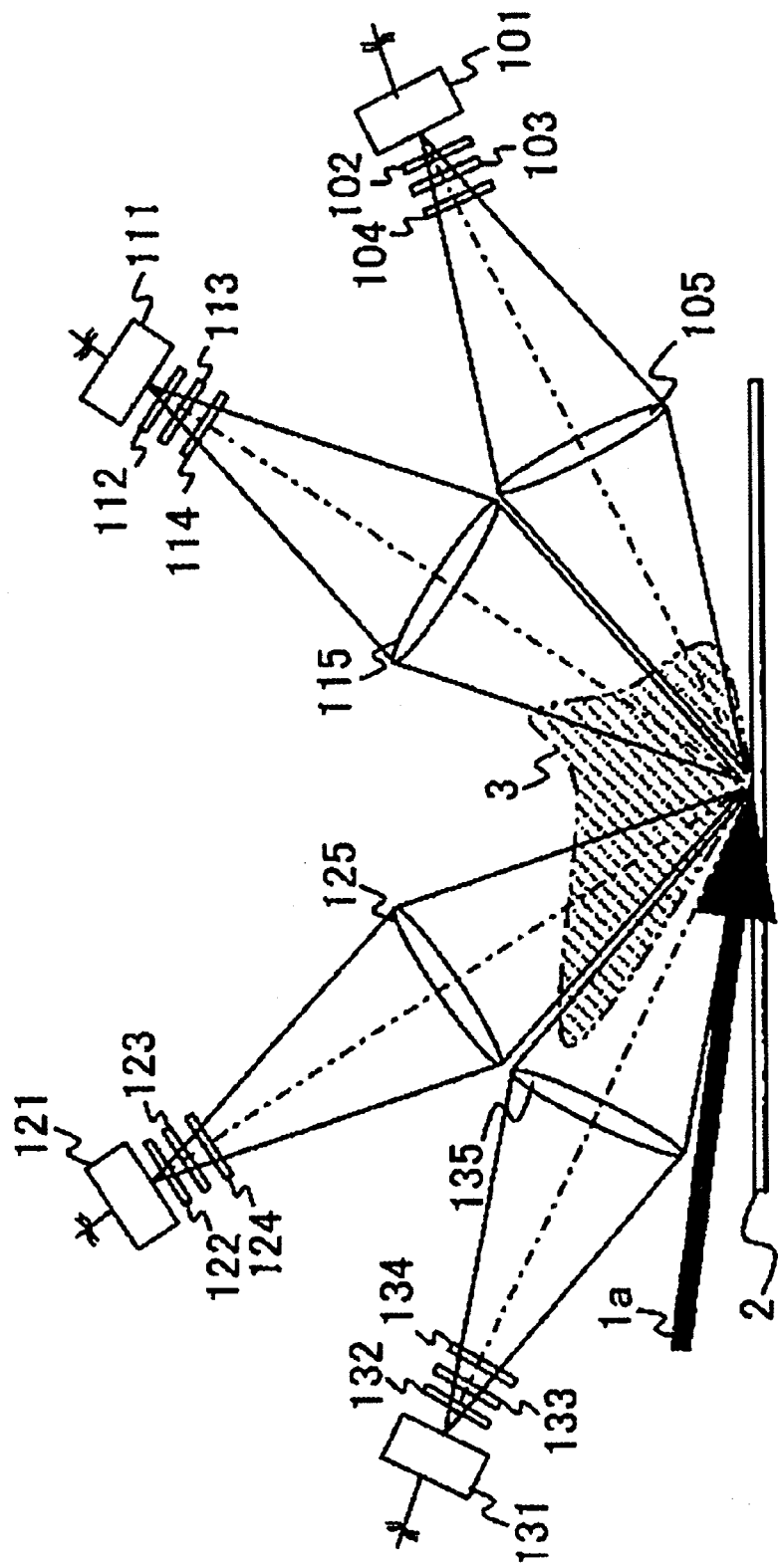
FIG. 4 is a view showing one example of a detecting element having four detecting optical systems.

The detecting optical system 1002 as shown in FIG. 1 is composed of two detecting optical systems, and appropriately comprises the lenses 105 and 115 for condensing the scattered light or reflected light that is radiated at a certain azimuth or elevation angle from the inspection object substrate 2 due to the light applied by the illuminating optical system 1001 for a predetermined numerical aperture (NA), the analyzers 104 and 114 for extracting any polarized light component only from the condensed scattered light or reflected light, the band pass filters 103 and 113 for reducing a stray light, the neutral density filters 102 and 112 for adjusting the light quantity, and the sensors 101 and 111. Herein, an instance of using two detecting optical systems having different elevation angles has been described above, but alternatively, four detection systems may be provided at different elevation angles, as shown in FIG. 4. In the invention, it is important that the detecting optical systems may be provided at a plurality of azimuth or elevation angles, as will be described later.

Herein, the sensors 101 and 111 are elements for converting the incident light into a voltage or current for output, and may be a photomultiplier or CCD sensor. If the photomultiplier is employed as the sensor, the multiplication factor (gain) of the signal is adjusted in accordance with a dynamic range of the signal processing system 1004 at the latter stage of the sensor or a scattered light quantity of the inspection object substrate 2. Though a detection example of the light by combination of lens and sensor has been described above in the detecting optical system 1002 as shown in FIG. 1, it is necessary that the light radiated at a plurality of azimuth or elevation angles may be detected by the sensors independently, and a combination of a mirror or a diffractive light element may be employed.

Next, the signal processing system 1004 for making the defect determination and surface roughness determination will be described below. The signal processing system 1004 appropriately comprises the preamplifiers 151 and 161 for amplifying a detection signal from each sensor 101, 111 in the plurality of detecting optical systems, and a signal processing circuit section 30 for performing the required amplification, a noise process and an analog to digital conversion process. Particularly if the photomultiplier is employed as the sensor 101, 111, the preamplifiers 151 and 161 are used because the output is a weak current. The outputs from the preamplifiers 151 and 161 are processed independently or by adding the signals in the signal processing section 30.

Herein, FIG. 3 shows one example of the signal (current or voltage) detected by the sensor, in which the horizontal axis represents the time (or position because the radial scanning is made) and the vertical axis is indicated with the detected light intensity or signal value. A detection signal of the scattered light quantity caused by a defect on the substrate surface and a detection signal caused by a surface state of the substrate are detected at the same time, as shown in FIG. 3A. By extracting a specific frequency component only in the signal processing circuit section 30, it is possible to separate a signal of high frequency as a defective signal (FIG. 3B) and a signal of low frequency as a wafer surface state signal (FIG. 3C), and thereby employ the signal in the high frequency band for defect detection and the signal in the low frequency band for surface state detection. Also, the signal processing section 30 has a function of adding the signals in the plurality of detecting optical systems. The addition of signals in the plurality of detection systems may be made in a digital processing section, not an analog processing section. Besides, in the digital processing section of the signal processing section 30, a threshold value is set to the signal in the high frequency band, and the signal beyond the threshold value is detected as the defect, whereby the detection signal value and existence position (position in the R-θ coordinates) at that time are stored in a storage section 60 at the latter stage. Also, for the signal in the low frequency band, the signal value is detected as the surface state detection value, and the detection signal value and existence position are stored in the storage section 60 at the latter stage. For the signal added in the analog processing section, the same process is conducted to detect the defect and the surface state. In the section for adding the signals from the different detection systems, the gain and offset are adjusted depending on an individual difference of the sensor or analog board before addition. Also, any sensor of the plurality of sensors may be increased in the gain for defect detection (e.g., application voltage is increased in the photomultiplier) to make the inspection, in which case the signal processing board for the surface state measurement is adjusted so that the gain of each sensor may be apparently equal, that is, the gain of the circuit board for the sensor with increased gain may be decreased and conversely the gain of the circuit board may be increased if the gain of the sensor is low. Though two signals are added in this embodiment, the number of signals is not necessarily limited to two, and any number of signals may be added, or the signals may be added after adjustment of signal in each detection section at any ratio in making the addition.

Next, a software processing control section 50 will be described below. In the software processing control section 50, an additional functional post-processing is performed for the detected defect signal or surface state signal. For example, the defect size calculation, the defect classification, and the conversion of the surface state signal into the RMS value may be performed. If the data of the film materials or film thickness is provided beforehand, the size calculation at high precision, the classification and the conversion into the RMS value can be made by using the data. Though not shown, the control of the illuminating optical system 1001, the stage scanning section 1003, the sensor gain and the circuit board is also performed in the software processing control section 50. The software processing control section 50 is configured by a personal computer, and connected to the storage section 60, input means 70 and display means 80. Also, it is connected to communication means for connecting to the host system or relevant system and has a function of controlling the overall system.

Referring now to FIGS. 5 to 8, the relationship between the detection system and the surface roughness of the inspection object substrate will be described below.

Figure 5A:
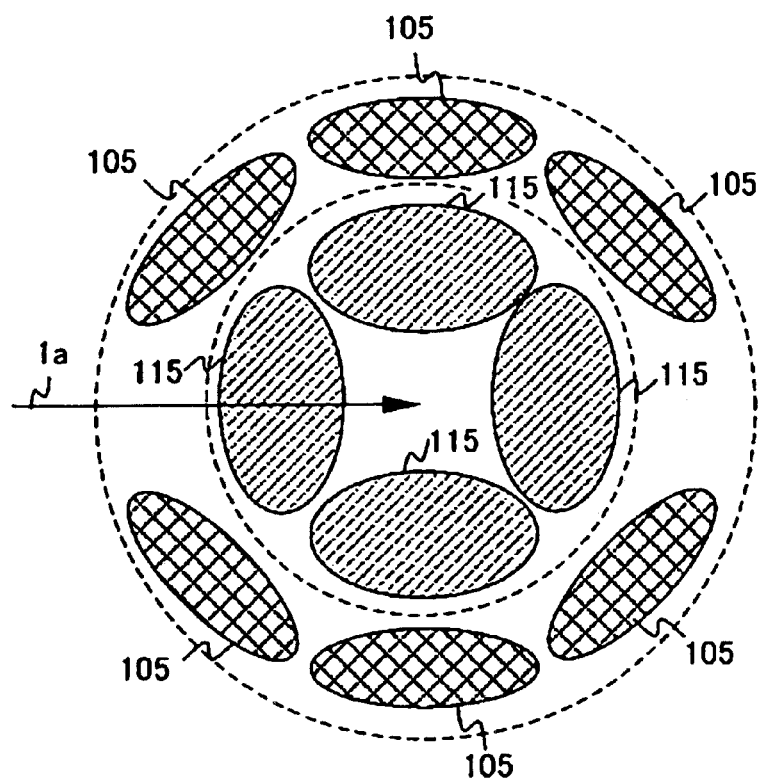
FIG. 5A is an upper view showing one example of the numerical aperture in the detecting element having a plurality of detection systems.
Figure 5B:
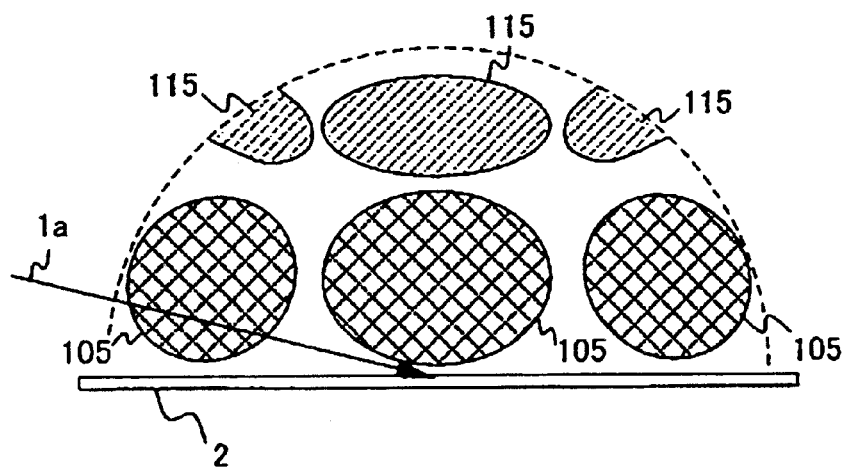
FIG. 5B is a side view showing one example of the numerical aperture in the detecting element having the plurality of detection systems.

FIG. 5 shows the numerical aperture (NA) of the detection section composed of the four detection systems arranged at the first elevation angle and mutually different azimuth angles and the six detection systems arranged at the second elevation angle and mutually different azimuth angles as one example of the detection section, wherein FIG. 5A is its upper view and FIG. 5B is its side view. The following explanation is given taking this detection section as an example, as needed.

FIG. 6 shows the correspondences between the detection system and the surface roughness of the inspection object substrate in the frequency space. Assuming that the wavelength of illumination is λ, the incident angle is θi, the detection angle of the detection system is θs and the azimuth angle is ϕs, the relationship between the frequency of surface roughness and the position of the detection system is represented based on the relationship of light diffraction in the following expression.

$$f_x = \frac{\sin\theta_s \cos\phi_s - \sin\theta_i}{\lambda} \quad \text{[Numerical expression 1]}$$

$$f_y = \frac{\sin\theta_s \sin\phi_s}{\lambda} \quad \text{[Numerical expression 2]}$$

Figure 6A:
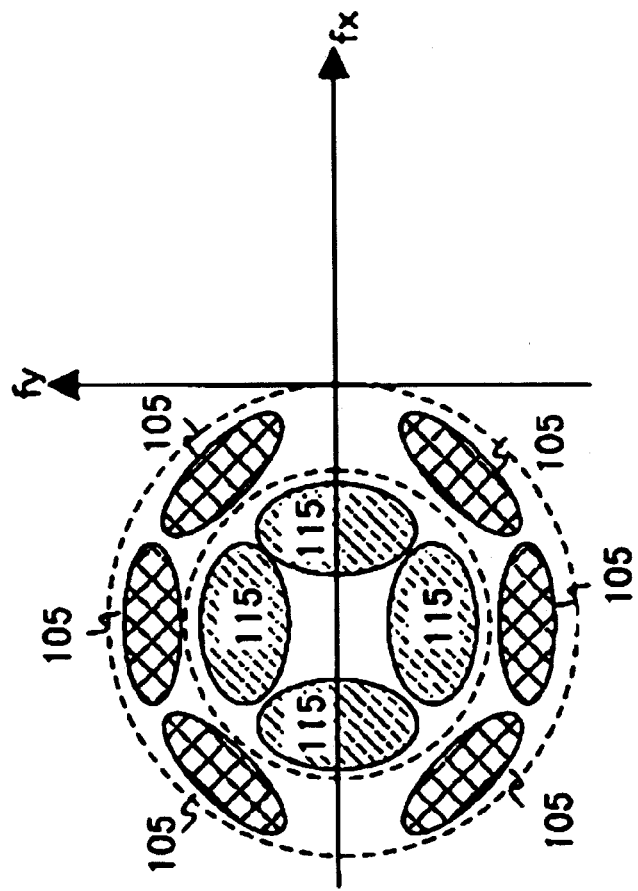
FIG. 6A is a view showing a frequency band distribution detectable in applying the light vertically to the inspection object substrate.
Figure 6B:
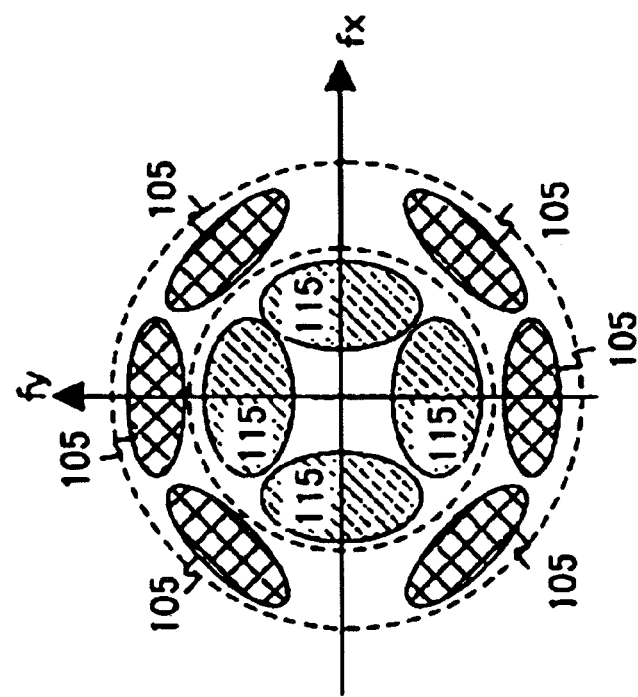
FIG. 6B is a view showing the frequency band distribution detectable in applying the light obliquely to the inspection object substrate.

FIG. 6A shows a frequency band distribution detectable in applying the light vertically (θi=0) to the inspection object substrate and FIG. 6B shows a frequency band distribution detectable in applying light obliquely (θi=80) to the inspection object substrate, taking the case of FIG. 5 previously described as an example. As will be clear from the above expression and FIG. 6, the specific frequency band is only detectable among the frequency components of the substrate surface roughness, in which the detectable frequency band is wider as the incident angle of illumination is larger. Also, if the plurality of detection systems are provided, the plurality of specific frequency bands only can be detected independently.

Figure 7A:
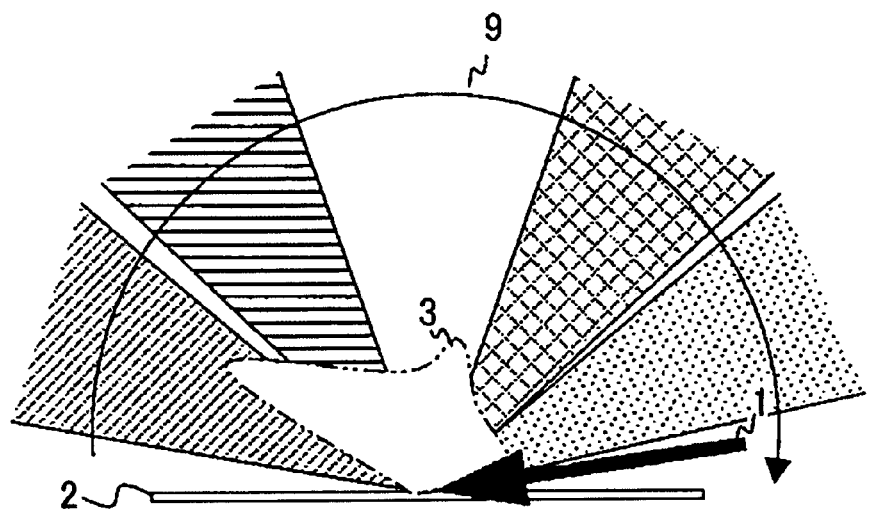
FIG. 7A is a view showing the frequency band distribution of surface roughness detectable by each detector in the four detection systems having different detection angles.
Figure 7B:
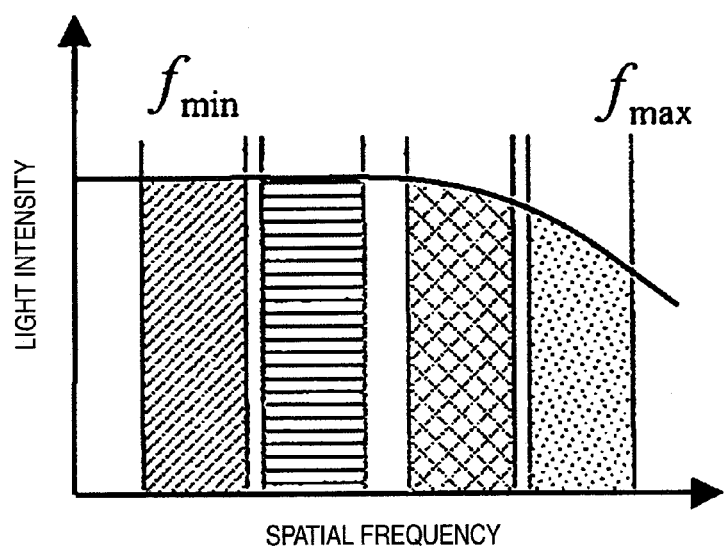
FIG. 7B is a view showing the relationship between the light intensity of is substrate surface roughness and the frequency band detectable by each detector in a case where there are four detection systems having different detection angles.

FIG. 7 shows the relationship between the detection system and the surface roughness of the inspection object substrate in the frequency space from another viewpoint of FIG. 6. FIG. 7A shows the frequency components of surface roughness detectable in each detection system, using an instance where there are four detection system having different detection angles as previously described and shown in FIG. 4. If the illuminating light 1 is incident at the incident angle θi of about 80 degrees upon the inspection object substrate 2, the detector closer to the reflected light of illumination detects the low frequency component of substrate surface roughness and the other detectors detect the higher frequency components in order clockwise in FIG. 7A. FIG. 7B shows the relationship between the light intensity (detection signal) of substrate surface roughness and the frequency band detectable in the detection system.

Herein, since the light quantity detectable in the detection system is detected by condensing (i.e., integrating) the scattered light corresponding to the specific frequency band, the square of the RMS value of substrate surface roughness is the integral value of power spectrum in the specific frequency band, and the energy of signal waveform is conserved before and after the Fourier transformation (Parseval's theorem), it follows that the square value of the RMS value and the detected light quantity compute the scalar quantity of the same quality by combining the frequency bands for the detection system and in computing the RMS value. That is, it is indicated that the RMS value of substrate surface roughness can be calculated from the detected light quantity corrected by the light quantity of illumination, the reflectance of the substrate or the gain of the detection system. From the above, the RMS value of substrate surface roughness corresponding to the specific frequency band only can be detected by independently calculating the surface state based on the scattered light quantity detected in each of the detection systems. Also, the RMS value corresponding to the overall frequency band detectable in the detection systems can be detected by adding the scattered light quantity in each of the detection systems.

Figure 8A:
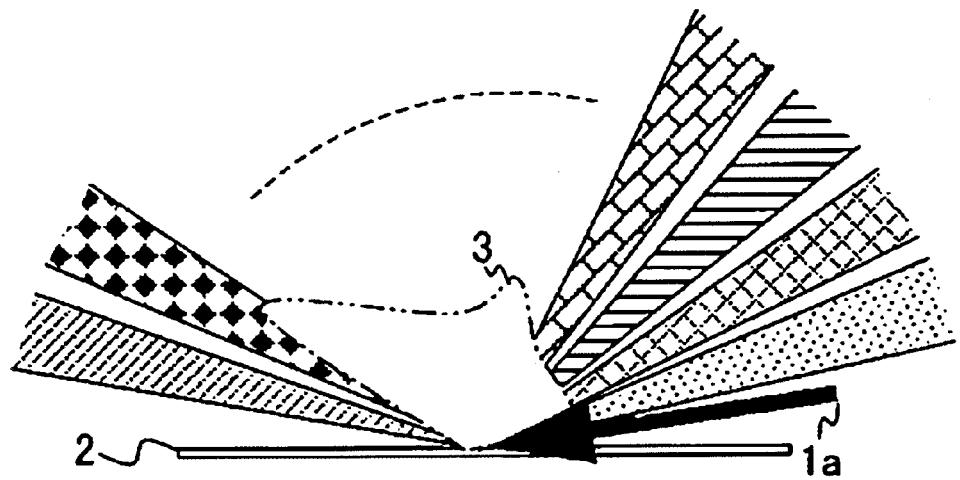
FIG. 8A is a view showing the frequency band distribution of surface roughness detectable by each detector in five or more detection systems having different detection angles.
Figure 8B:
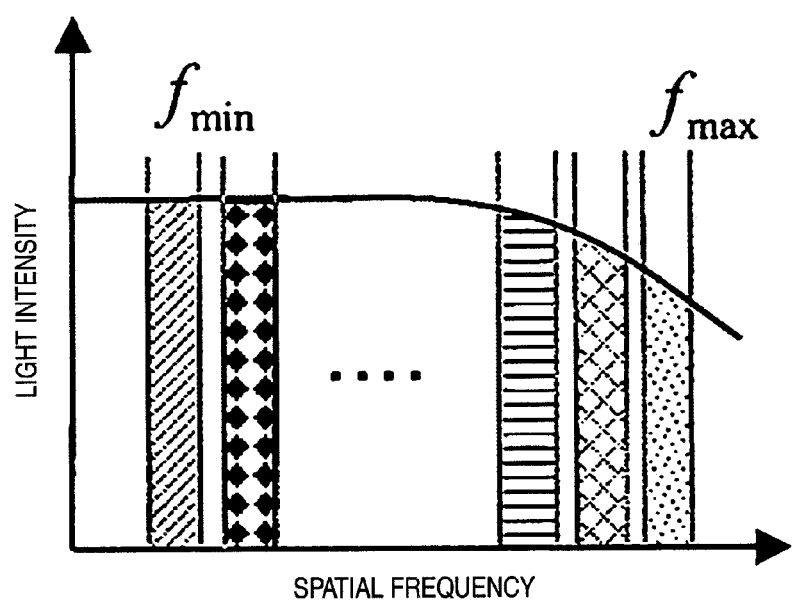
FIG. 8B is a view showing the relationship between the light intensity of substrate surface roughness and the frequency band detectable by each detector in a case where there are five or more detection systems having different detection angles.

FIGS. 8A and 8B, like FIG. 7, show the relationship between the detection system and the surface roughness of the inspection object substrate in the frequency space, in which more detection systems are disposed than in FIG. 7. With more detectors, more accurate frequency information can be acquired.

Figure 9:
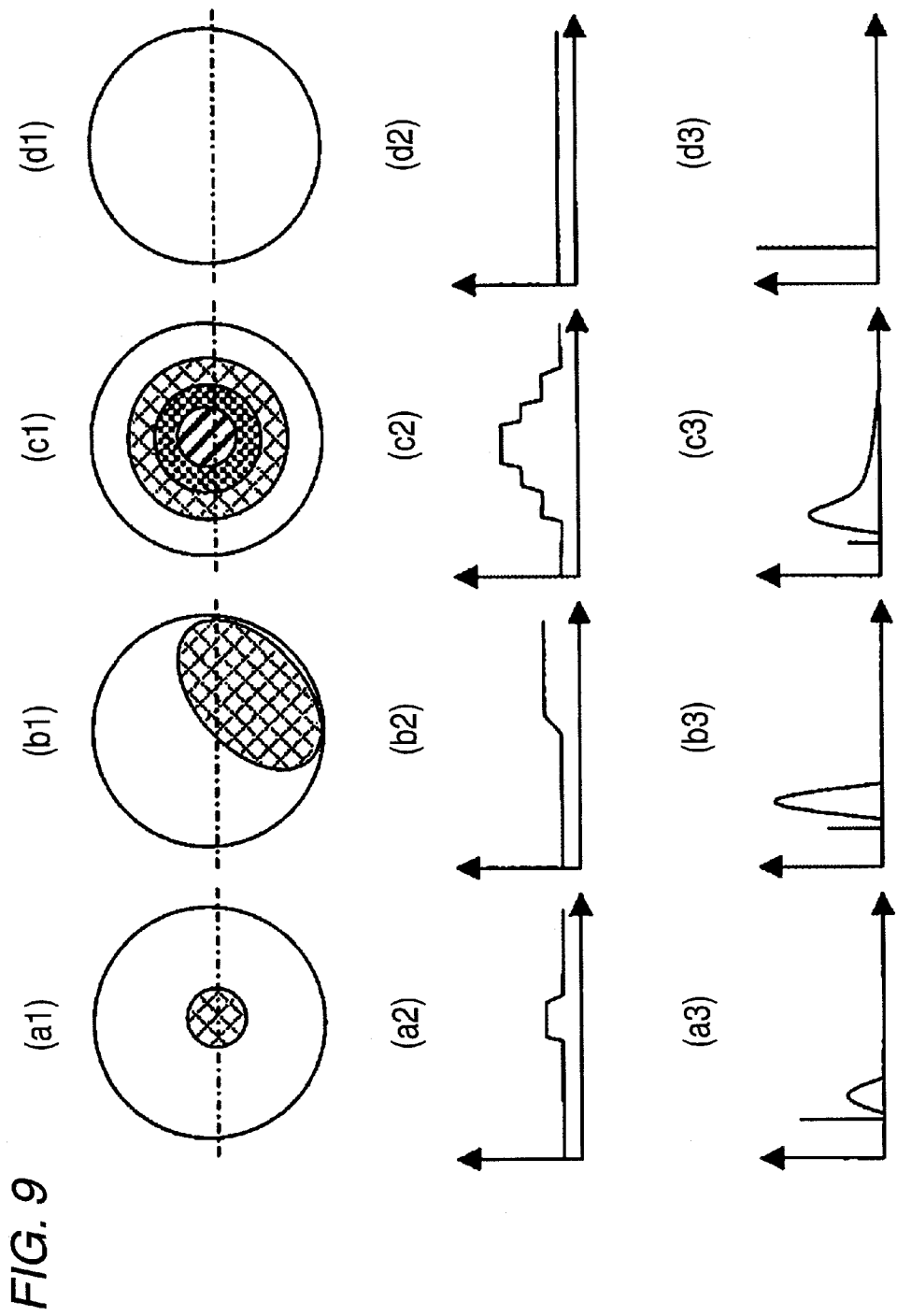
FIG. 9($a$1) is a first view showing one example of a surface state map.

Herein, a display example of the detected surface state detection value or RMS value for each frequency band is shown for the entire surface of the substrate based on the coordinate information in FIG. 9. FIG. 9($a1$) shows a surface state map, FIG. 9($a2$) shows a cross-sectional waveform of the surface state detection value or RMS value, and FIG. 9($a3$) shows a frequency distribution of the surface state detection value or RMS value on the entire surface of the substrate. FIGS. 9($b1$) to 9($b3$), FIGS. 9($c1$) to 9($c3$) and FIGS. 9($d1$) to 9($d3$) show the surface state map, cross-sectional waveform and frequency distribution of the wafers having different surface states in the same way.

Figure 10:
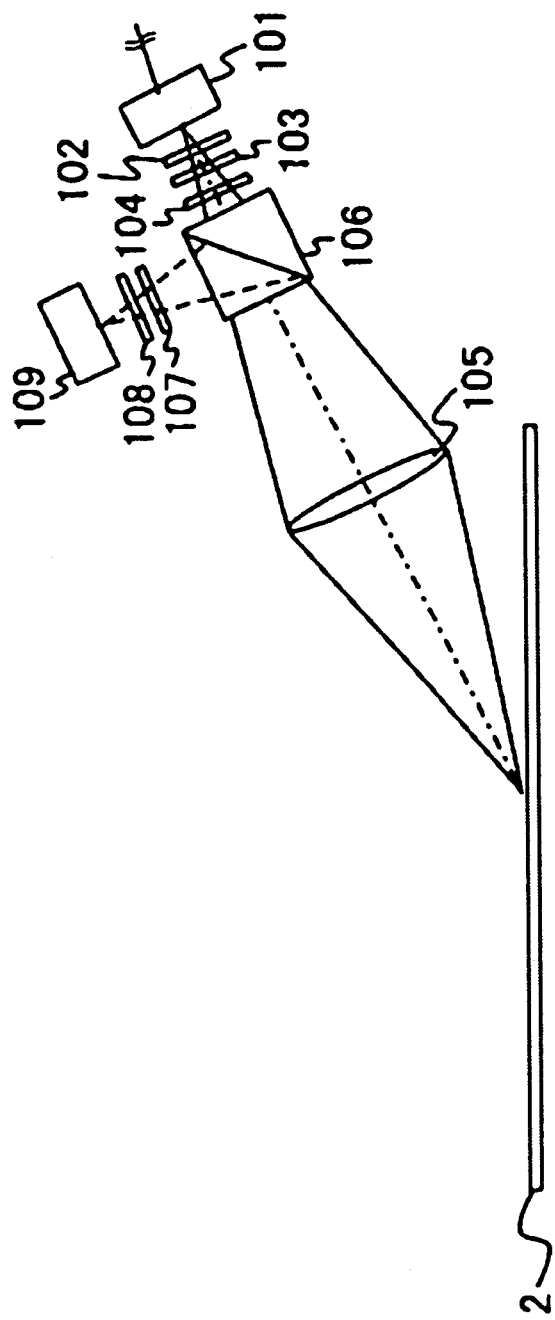
FIG. 10 is a view showing an embodiment of a detection system in which the detecting optical path is separated.
Figure 11:
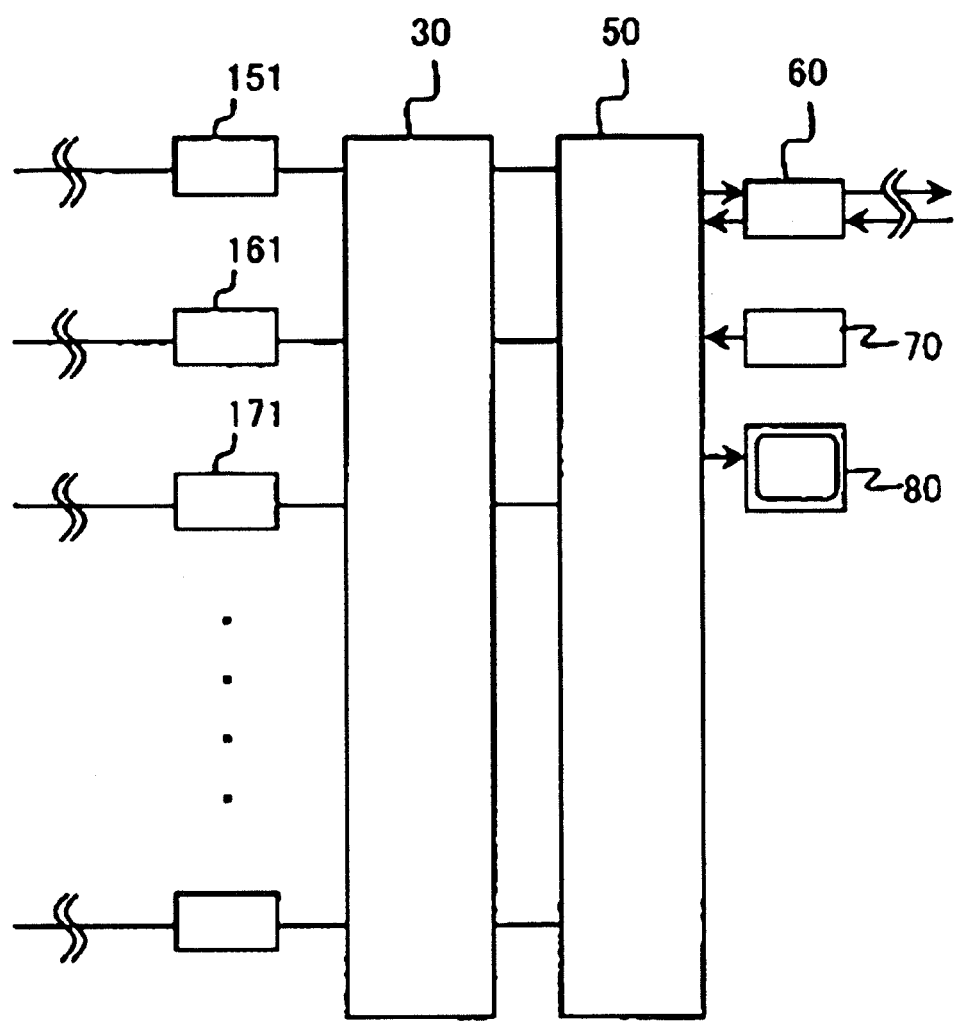
FIG. 11 is a view for explaining the configuration of a signal processing section in an inspecting apparatus according to the invention.

Referring to FIG. 10, an embodiment of the detection system for making the defect inspection and the surface state inspection at the same time will be described below. For the defect inspection, it is required to remove the scattering on the wafer surface as much as possible to increase the S/N, and it is effective to reduce and detect the scattered light from the wafer surface using an analyzer. On the other hand, in inspecting the wafer surface state, it causes negative effect that the light is removed by the analyzer. Thus, a beam splitter 106 is mounted to split the light into two optical paths for defect detection and surface state detection, and the analyzer 104 is disposed on only one optical path, as shown in FIG. 10, whereby both functions can be achieved at the same time. In this case, a signal processing circuit for defect detection may have a high pass filter alone, and a signal processing circuit for surface state detection may have a low pass filter alone.

Figure 12:
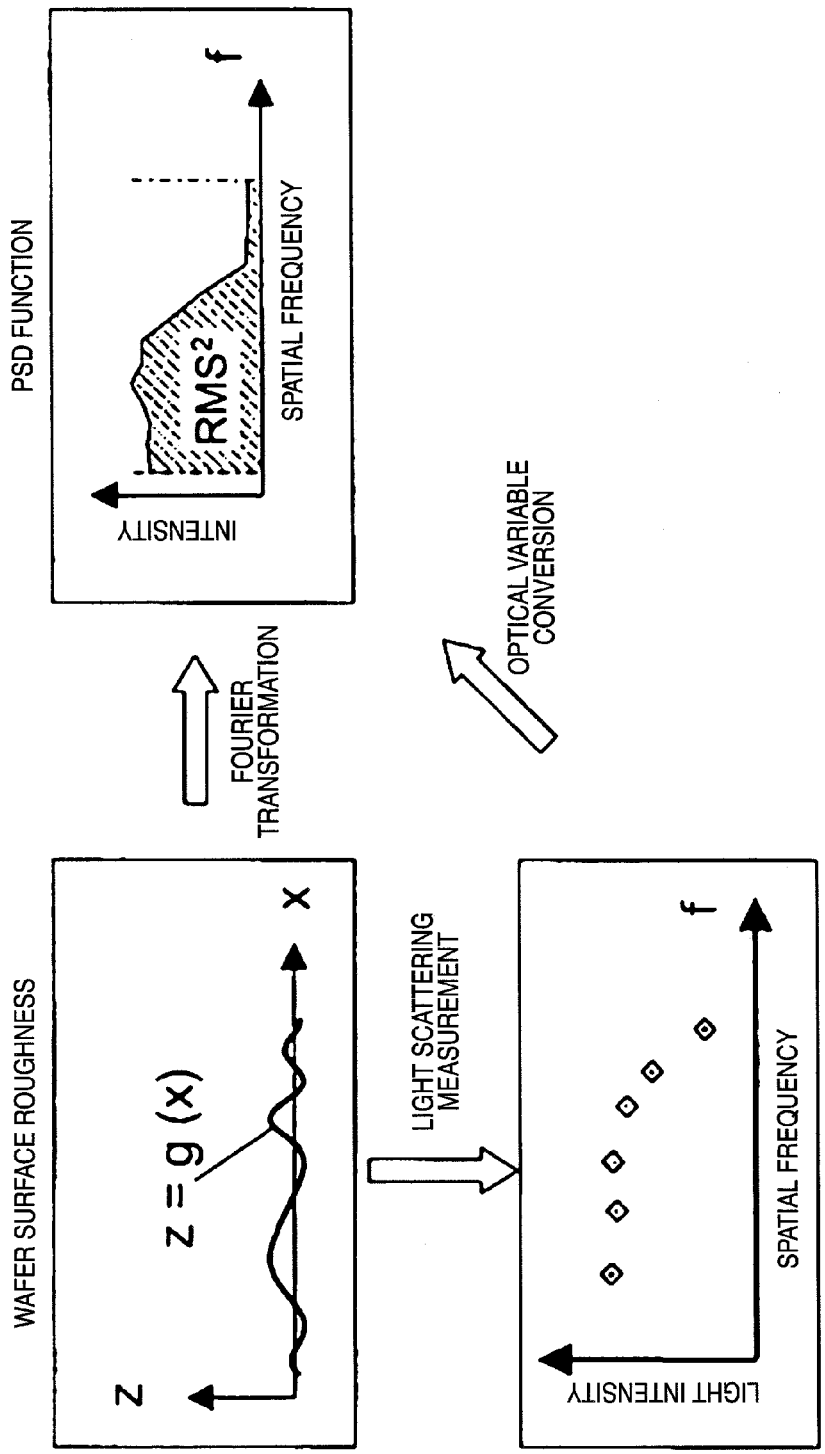
FIG. 12 is a view showing the correlation between surface roughness, RMS(Rq) and apparatus output.

Referring to FIG. 12, the relationship between the surface roughness of wafer and the RMS will be described below. Though the measurement of the wafer surface is made in three dimensions, the explanation is given here in two dimensions for simplicity. First of all, the surface roughness of wafer is represented in the following expression, using the position x and the height z.

$$z=g(x)$$ [Numerical expression 3]

At this time, the constant term of the function g(x) is adjusted so that the average height of wafer may be z=0. Making the Fourier transformation of the function g(x), the function is transformed into the frequency space. The function F(g(x)) after the Fourier transformation at this time is generally called a PSD function.

Herein, the square value of the RMS(Rq) value is the integration of the average value (i.e., z=0) of the function g(x). Also, owing to the Parseval's theorem, the integral value of g(x) and the integral value of the PSD function after the Fourier transformation are equal, whereby the RMS value can be computed if the PSD function is known.

On the other hand, for the light scattering on the wafer in the surface shape with z=g(x), if the scattered light is detected in the plurality of detecting optical systems disposed at different positions, and the signal to be extracted in the frequency band preprogrammed in accordance with the position of the detector is extracted and measured from the obtained detection signal, as already described, the output very similar to the PSD function can be detected. This output is the value of the PSD function multiplied by the optical constant of wafer and the conditions (wavelength, polarization) of the optical system in the form of function, as described in non-patent document 1 (APPLIED OPTICS 1995 Vol. 34, No. 1 pp. 201-208). The conditions of the optical system, which are known information for the apparatus creator, can be easily obtained. Also, the optical constant of wafer is usable by acquiring beforehand the data for each wafer to be inspected. To acquire beforehand the data, there are a method for making the measurement in creating the inspection conditions, a method for inputting the data measured in another apparatus, a method for making the measurement for each inspection, and a method for prestoring the film materials and the reflectance data in the storage section 60.

As described above, the signal obtained by the light scattering measurement is firstly converted into the PSD function, and the PSD function is further integrated, whereby the RMS (Rq) value can be calculated.

Figure 13B:
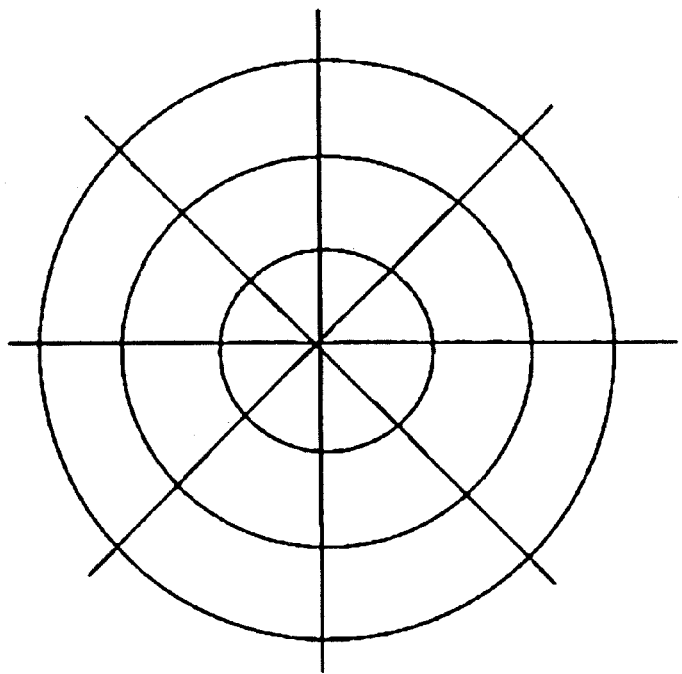
FIG. 13B is a second view showing an example in which the substrate surface is spatially divided into areas.
Figure 13A:
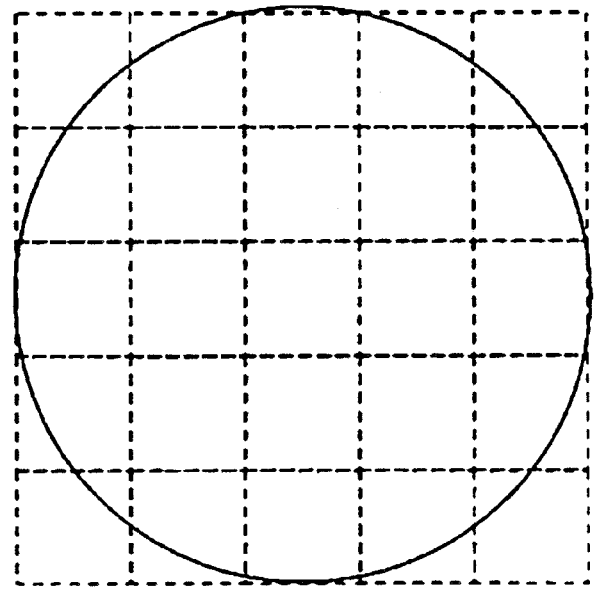
FIG. 13A is a first view showing an example in which the substrate surface is spatially divided into areas.

Next, a space dividing example of the inspection object surface required in evaluating the inspection result of the surface state will be described below. In the defect inspection, the general condition of wafer may be grasped based on the statistic such as the number of defects, in addition to the position, size and kind of defect, and in the surface state inspection of wafer, if there is the similar statistic, it is easier to grasp the general condition. Thus, if the upper limit value of the surface state inspection signal or the RMS is preset by dividing the space in the form of FIG. 13A or 13B, it is possible to monitor the space dividing point or its number in the area exceeding the upper limit value on the entire surface of wafer.

Figure 14:
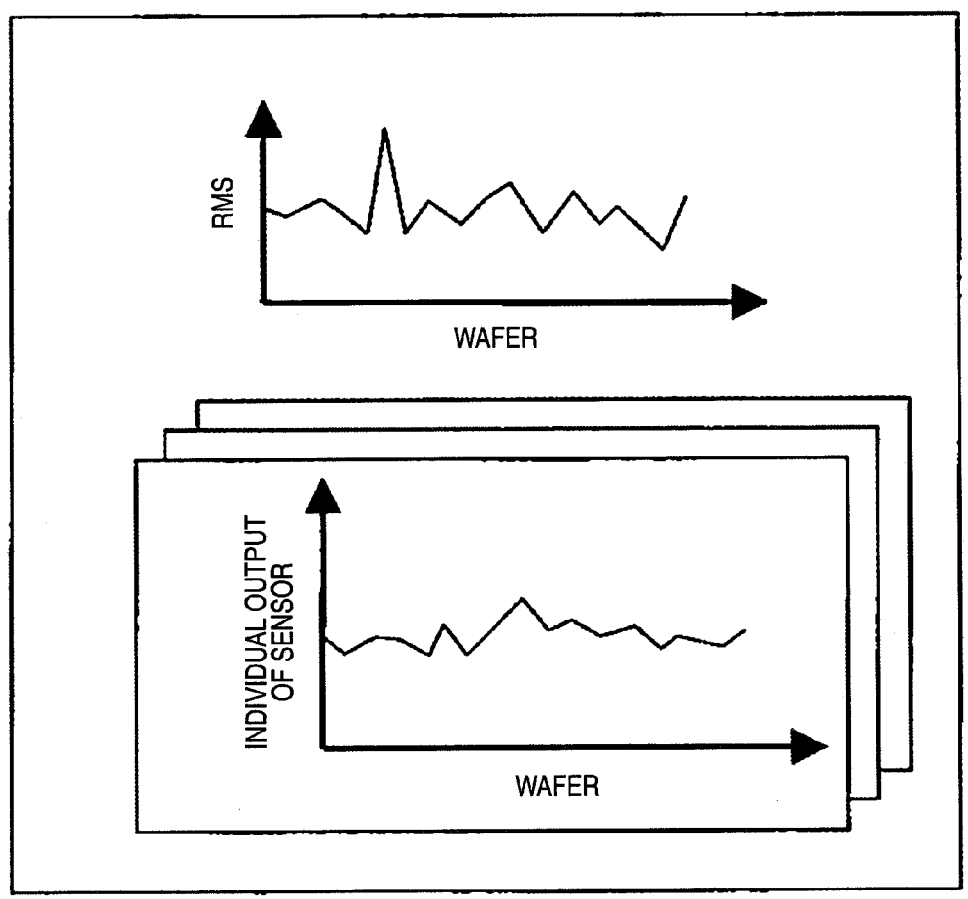
FIG. 14 is a view showing one example of trend data in a wafer surface state.

FIG. 14 shows one example of trend data in the surface state of wafer. On display means 80, the average RMS value on the entire surface of wafer, the average output value of each sensor, or the number of areas exceeding the upper limit value on the entire surface of wafer as previously described are displayed successively for each wafer, whereby the state of wafer can be is grasped in time series.

In connection with FIG. 4, the scattering of light owing to particles on the substrate can be represented in the following expression [non-patent document 2 (P. A. Bobbert and J. Vlieger (Leiden Univ.): Light Scattering)].

$$BRDF = \frac{16\pi^4}{\lambda^4}\left(\frac{n_{sph}^2 - 1}{n_{sph}^2 + 2}\right)^2 \frac{NF}{A} \frac{a^6}{\cos\theta_s \cos\theta_i}|Q^{part} \cdot \hat{e}|^2 \qquad \text{[Numerical expression 4]}$$

Figure 15:
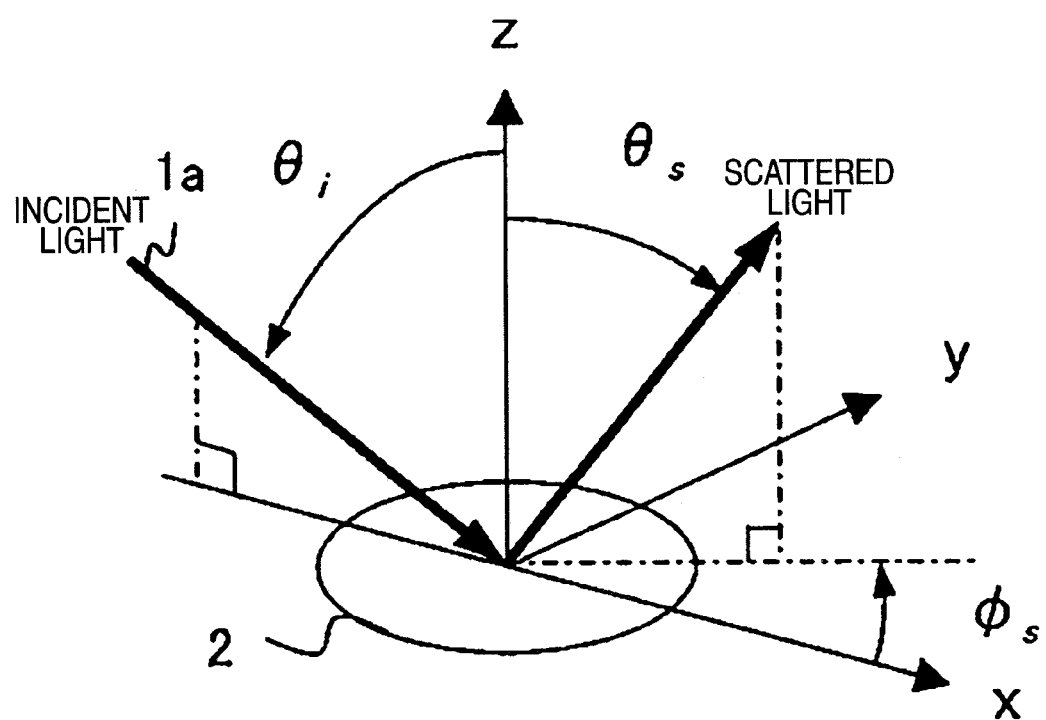
FIG. 15 is a coordinate system in a BRDF calculation expression.

Herein, the BRDF, which is called a bidirectional reflectance distribution function, is a function inherent to the reflection spot, representing how much light quantity is reflected in each direction when the light is incident on a certain spot x on the reflecting (scattering) surface from a certain direction. In a rough representation, the reflectance is generalized.

Wherein $\pi$ is the ratio of the circumference of a circle to its diameter, $\lambda$, is the illumination wavelength (μm), $n_{sph}$ is the refractive index of particle, N/A is the density (number/μm) of particles within the illumination area, and F is a structure factor depending on the positional relationship of the noticed scatterer with another scatterer existing nearby. If the scatterers exist randomly, F=1. Also, a is the radius (μm) of particle, θs and θi are the detection angle and the incident angle (degree), and $\hat{e}$ is a unit vector of incident light in the electric field direction. The coordinate system is shown in FIG. 15, which is an explanation view of variables for use in the numerical expression of the BRDF (bidirectional reflectance distribution function) as previously described. $Q^{part}$ is the parameter of polarization, and has the following four combinations of incident light and detected polarized light. $Q_{SP}$ means the S polarization incidence and P polarization detection.

$$Q_{ss} = [1+\beta r_s^{12}(\theta_s)][1+\alpha r_s^{12}(\theta_i)]\cos\phi_s$$

$$Q_{sp} = -[1+\beta r_p^{12}(\theta_s)][1+\alpha r_s^{12}(\theta_i)]\cos\theta_s\sin\phi_s$$

$$Q_{ps} = -[1+\beta r_s^{12}(\theta_s)][1-\alpha r_p^{12}(\theta_i)]\cos\theta_i\sin\phi_s$$

$$Q_{pp} = [1+\beta r_p^{12}(\theta_p)][1+\alpha r_p^{12}(\theta_i)]\sin\theta_i\sin\phi_s - [1-\beta r_p^{12}(\theta_s)][1-\alpha r_p^{12}(\theta_i)]\cos\theta_s\cos\theta_i\sin\theta_s \qquad \text{[Numerical expression 5]}$$

Wherein $\alpha = \exp(ika \cdot \cos\theta_i)$ is the phase difference corresponding to the optical path length difference between the incident light and the reflected light, and $\beta = \exp(ika \cdot \cos\theta_s)$ is the phase difference corresponding to the optical path length difference between the scattered light and the reflected light without being scattered. Also, $r_p^{12}(\theta)$ and $r_s^{12}(\theta)$ are the Fresnel's formulas for reflection, represented in the following expressions. The superscript 12 denotes the reflection factor on the medium 1 and the medium 2, and the subscripts p and s mean the P polarization and the S polarization. The circularly polarized light and the elliptically polarized light are considered in the S polarization component and the P polarization component.

$$r_p^{12}(\theta) = \frac{(n_2/n_1)^2\cos\theta - [(n_2/n_1)^2 - \sin^2\theta]^{1/2}}{(n_2/n_1)^2\cos\theta + [(n_2/n_1)^2 - \sin^2\theta]^{1/2}} \qquad \text{[Numerical expression 6]}$$

$$r_s^{12}(\theta) = \frac{\cos\theta - [(n_2/n_1)^2 - \sin^2\theta]^{1/2}}{\cos\theta + [(n_2/n_1)^2 - \sin^2\theta]^{1/2}}$$

Also, the light scattering due to the surface roughness of the substrate can be represented in the following expression [non-patent document 3 (S. O. Rice, Comm. Pure and Appl. Math 4, 351 (1951))].

$$BRDF = \frac{16\pi^2}{\lambda^4}\cos\theta_s\cos\theta_i S(f) \times |Q^{topo} \cdot \hat{e}|^2 \qquad \text{[Numerical expression 7]}$$

The BRDF is a bidirectional reflectance distribution function as described in the section of the light scattering owing to the particles. S(f) is called the PSD function, representing the power spectrum in considering that the substrate surface is composed of a combination of surface structures at various frequencies. $Q^{topo}$ is the parameter of polarization and has the following four combinations with the incidence and detection polarization. $Q_{SP}$ means the S polarization incidence and the P polarization detection. In the film of which the surface is optically opaque, $Q_{topo}$ is as follows.

$$Q_{ss} = Q_{s0}\cos\phi_s$$

$$Q_{sp} = -Q_{s0}(n_{mat}^2 - \sin\theta_s)^{1/2}\sin\phi_s$$

$$Q_{ps} = Q_{p0}(n_{mat}^2 - \sin\theta_i)^{1/2}\sin\phi_s$$

$$Q_{pp} = -Q_{p0}[n_{mat}^2\sin\theta_i\sin\phi_s - (n_{mat}^2-\sin\theta_i)^{1/2}(n_{mat}^2-\sin\theta_s)^{1/2}\cos\phi_s] \qquad \text{[Numerical expression 8]}$$

Wherein $n_{mat}$ is the refractive index of the substrate.

$$Q_{s0} = \frac{n_{mat}^2 - 1}{[\cos\theta_i + (n_{mat}^2 - \sin\theta_i)^{1/2}][\cos\theta_s + (n_{mat}^2 - \sin\theta_s)^{1/2}]} \qquad \text{[Numerical expression 9]}$$

$$Q_{p0} = \frac{n_{mat}^2 - 1}{[n_{mat}^2\cos\theta_i + (n_{mat}^2 - \sin\theta_i)^{1/2}][n_{mat}^2\cos\theta_s + (n_{mat}^2 - \sin\theta_s)^{1/2}]}$$

The light quantity to be detected may change depending on not only the substrate surface state S(t) but also the polarized state of illumination or polarization detection, and the conditions of the optical system such as the incident angle and azimuth angle of illumination and the elevation angle and azimuth angle of detection, as described above. Therefore, if the surface state of the substrate is evaluated by the light scattering under the same optical conditions, the relative evaluation is allowed, but if comparison is made under the different optical conditions, it is required to make the appropriate computation based on the above numerical expressions.

Besides, if a plurality of detectors are used and the scattered light is detected by changing the sensitivity or gain of each detector, it is required to make the appropriate correction for them.

Since the detecting optical system has the numerical aperture (NA), the is light scattering owing to the particles and the light scattering owing to the surface roughness are detected by condensing the light for NA in the detecting optical system (the BRDF function is integrated for NA).

Figure 16:
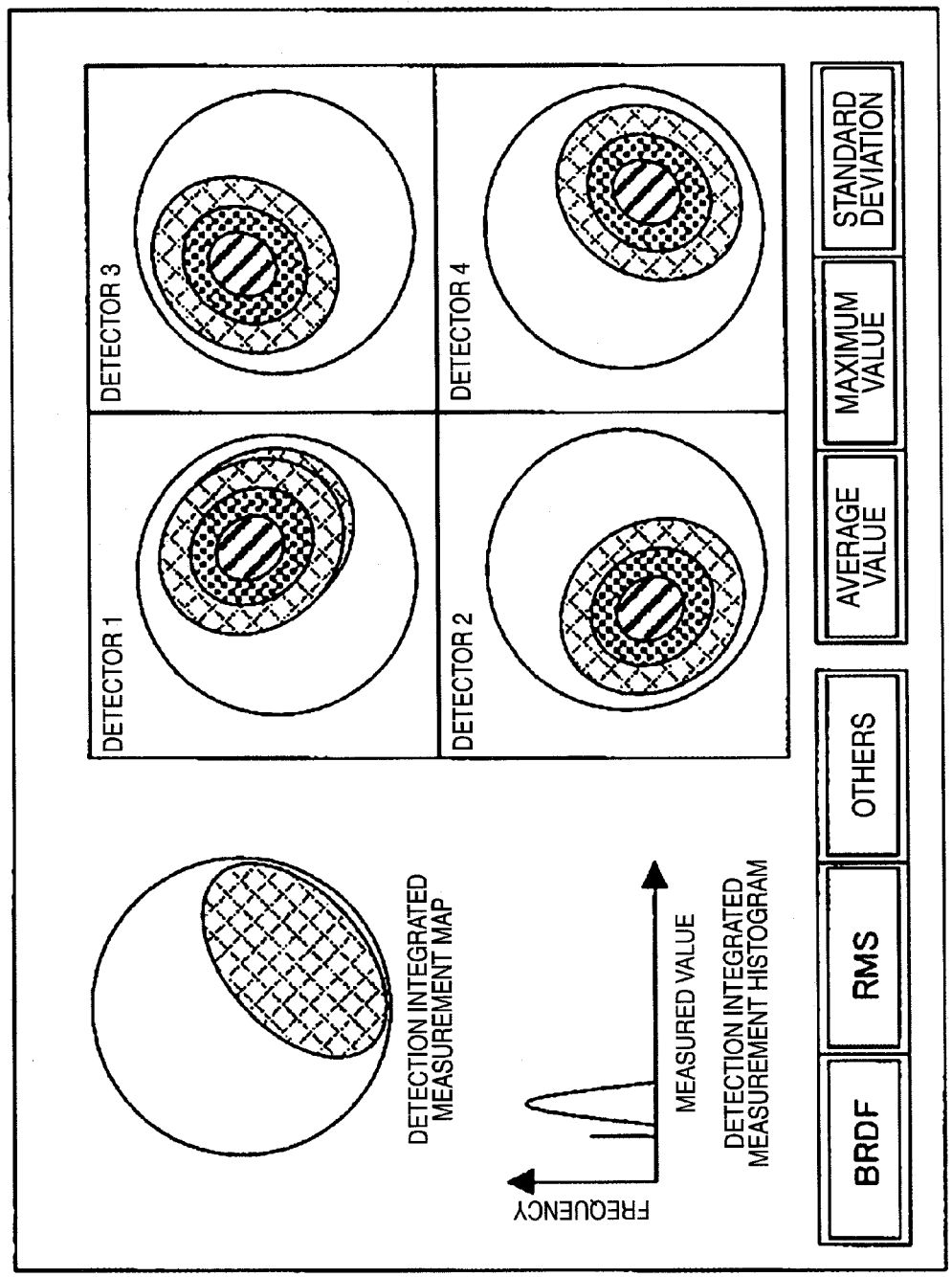
FIG. 16 is an example of measurement result outputs.

FIG. 16 shows the measurement results on the entire surface of the inspection object substrate in one example of the measurement result outputs. A detector integrated measurement map indicating the data added in analog or digital, the histogram information of the detector integrated measurement map and a detection map of each detector are illustrated. The BRDF value, the RMS value, and the film thickness value may be selectively outputted. Also, the statistic such as average value or maximum value may be displayed from each measurement result.

FIG. 17 shows the signal value of each detector for the inspection object substrate and a detection signal database of the substrate in which the surface roughness is known. For the substrate in which the surface roughness is known, the signal value of each detector is obtained beforehand by measurement or simulation and stored in the database. By comparison with the signal value of each detector for the inspection object substrate, the surface roughness of the inspection object substrate can be estimated.

Now, it is assumed that there are n detectors, and the signal value of each detector for the inspection object substrate is (s1, s2, s3, sn). On the other hand, it is assumed that the signal value of each detector for the substrate in which the surface roughness is known is (d11, d12, d13, d1$n$), (d21, d22, d23, d2$n$), . . . , and (dm1, dm2, dm3, dmn), the detection data of surface roughness can be represented as a multidimensional vector in which the signal value of each detector is the component. The degree of surface roughness of the inspection object substrate can be estimated by evaluating the degree of coincidence between the vector in the database and the vector of the inspection object substrate. If each surface roughness is associated with the RMS value in the database, the RMS value of the inspection object substrate can be estimated immediately.

Figure 18:
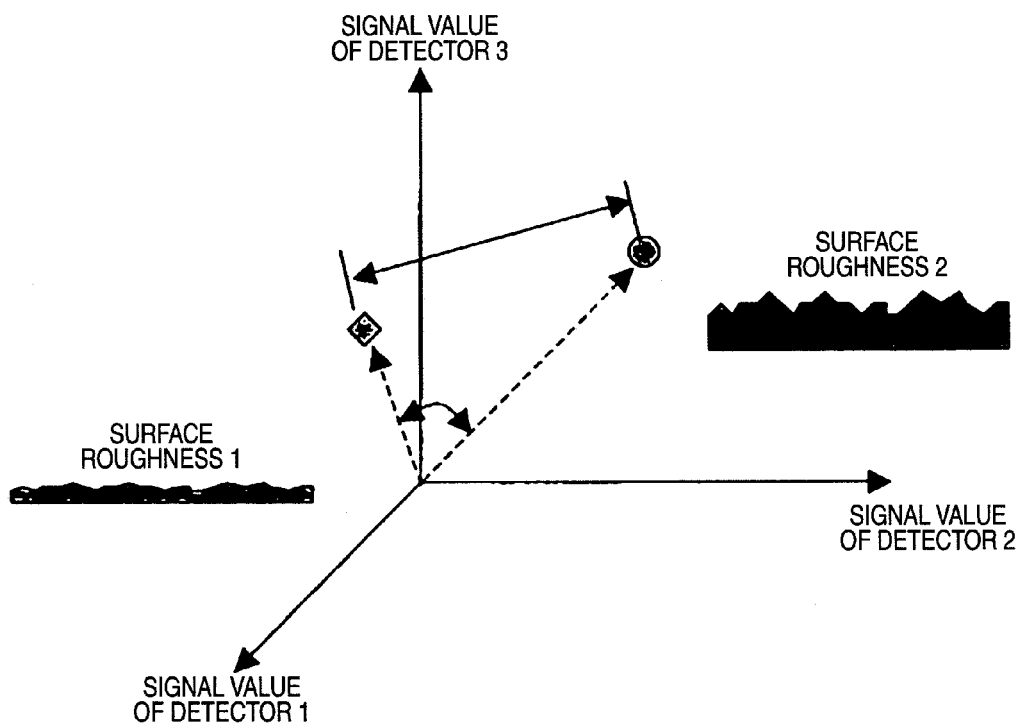
FIG. 18 is a view showing how the signal value for each detector is displayed in the three dimensional space.

FIG. 18 is a view plotting the detection signal value for two kinds of substrates having different surface states in the three dimensional space, supposing a case where there are three detectors for simplicity. As an evaluation index of the degree of coincidence of vectors, the Euclid distance between vectors, the weighted Euclid distance, or the angle between vectors may be employed. Also, the obtained detection signal is not directly made the component of vector, but once logarithmically converted, and the distance may be evaluated using the vector after logarithmic conversion.

A method with the Euclid distance between vectors as the evaluation index of the degree of coincidence of vectors will be described below as an example. It is supposed that there are the surface roughness 1 and the surface roughness 2 as the database, and the signal value of each detector for each roughness is (d11,d12,d13) and (d21,d22,d23). Now, it is supposed that when a sample in which the state of surface roughness is unknown (the surface roughness m is assumed here) is inspected, the signal of each detector is (dm1,dm2,dm3). Since the Euclid distance between vectors is the square root of the square sum of differences between components of the vector, the Euclid distance between the surface roughness m and the surface roughness 1 and the Euclid distance between the surface roughness m and the surface roughness 2 are represented in the following expressions.

Distance between surface roughness m and surface roughness 1 = $\sqrt{\sum_{k=1}^{3}(d1k - dmk)^2}$ [Numerical expression 10]

Distance between surface roughness m and surface roughness 2 = $\sqrt{\sum_{k=1}^{3}(d2k - dmk)^2}$ [Numerical expression 11]

The smaller one of the distances obtained in this way is employed as approximate data of the surface roughness m.

Also, as another example, in the case of the weighted Euclid distance, the following expression is used in calculating the Euclid distance.

Distance between surface roughness m and surface roughness 1 = $\sqrt{\sum_{k=1}^{3} w_k (d1k - dmk)^2}$ [Numerical expression 12]

Distance between surface roughness m and surface roughness 2 = $\sqrt{\sum_{k=1}^{3} w_k (d2k - dmk)^2}$ [Numerical expression 13]

Wherein $w_k$ is the weighting coefficient vector. If the value of each component of $w_k$ is 1, the weighted Euclid distance is equal to the Euclid distance.

If the detection signal of the surface roughness is once logarithmically converted and the distance is calculated, the distance between the surface roughness m and the surface roughness 1 is represented in the following expression.

Distance between surface roughness m and surface roughness 1 = $\sqrt{\sum_{k=1}^{3} w_k (\log(d1k) - \log(dmk))^2}$ [Numerical expression 14]

As another example of the evaluation index of the degree of coincidence of vectors, the angle between two vectors may be used. From the formula of the inner product of any two vectors OA and OB, the following expression holds for the angle θ between two vectors.

$OA \cdot OB = |OA||OB|\cos\theta$ $\theta = \arccos(OA \cdot OB/|OA||OB|)$

From the above, the angle between the surface roughness m and the surface roughness 1 is represented in the specific expression as follows.

$\theta = \arccos[(d11 \cdot dm1 + d12 \cdot dm2 + d13 \cdot dm3)/\{\sqrt{(d11^2 + d12^2 + d13^2)} \cdot \sqrt{(dm1^2 + dm2^2 + dm3^2)}\}]$ [Numerical expression 16]

In this case, the angle between the vector of each surface roughness existing in the database and the vector m in which the surface roughness of inspection object is unknown is obtained, and the vector of the smallest value in the database is employed as approximate data of the surface roughness m.

Though the evaluation method for the degree of coincidence of vectors has been described above by way of example, a basic concept of the invention is to estimate the surface roughness based on the detection signals of the plurality of detectors, namely, the spatial distribution of the light scattering intensity, and the invention is not limited to the above embodiments, but needless to say, may be changed in various ways without departing from the spirit or scope of the invention.

Though the invention has been described above in the instance in which the surface roughness only is changed, the light scattering changes depending on not only the state of surface roughness, but also a difference of film materials on the top surface or a difference of film thickness if the film is transparent to the illumination wavelength. Thus, a database in which each of the surface roughness, film thickness and film materials is changed is created, and comparison is made with the signal value of each detector for the inspection object substrate, whereby the surface roughness, film thickness and film materials can be estimated at the same time.

The creation of the database is made by creating the reference samples and actually collecting the measurement data or making the simulation.

Figure 19A:
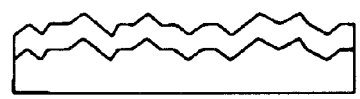
FIG. 19A is a first view showing the relationship in the shape between the top surface layer and its lower layer in a multilayer substrate.

The case of actually collecting the measurement data will be described below. A plurality of samples having the different states of surface roughness are prepared, as shown in FIG. 19A. The light scattering with each sample is measured beforehand, and the detection signal in each detector is prepared. For the samples having different states of surface roughness, the standard samples commercially available on the market may be used, and a method for changing the etching conditions such as blend of chemicals or etching time in etching the surface with the chemical solution, or a method for changing the polishing conditions such as polishing pressure or polishing time in polishing the surface may be used. In the film formation wafer, the film formation conditions such as temperature or pressure in forming the film may be changed.

A method of computation will be described below using FIGS. 18B and 18C. FIG. 18B is a view showing a method for measuring the prepared sample having different surface roughness with an AFM (atomic force microscope), computing the light scattering with the crenelation condition of the surface as input data, and storing it in the database. In the computation, instead of measuring the surface state of the sample with the AFM, a model of any surface state may be created and the light scattering may be computed to create the database. The computation methods for the light scattering in this case may include an FDTD method, and a DDA method, besides the BRDF method as previously described. FIG. 18C is a view showing the BRDF method. With the BRDF method, a PSD function for the surface roughness is used as an input variable for the light scattering computation, and a plurality of arbitrary PSD function models are created to compute the light scattering, thereby creating the database. In the BRDF method, $Q^{topo}$ is calculated depending on the film materials or film thickness, even for the sample having different film materials or film thickness, whereby the light scattering can be computed [non-patent document 4 (J. M. Elson: Light scattering from surfaces with a single dielectric overlayer; J. Opt. Soc. Am. 66, 682-694 (1976)), and non-patent document 5 (J. M. Elson: Infrared light scattering from surface covered with multiple dielectric overlayers; Appl. Opt. 16, 2872-2881 (1977)), 6].

$$BRDF = \frac{16\pi^2}{\lambda^4} \cos\theta_s \cos\theta_i S(f) \times |Q^{topo} \cdot \hat{e}|^2 \quad \text{[Numerical expression 17]}$$

Figure 19B:
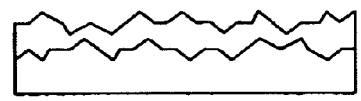
FIG. 19B is a second view showing the relationship in the shape between the top surface layer and its lower layer in the multilayer substrate.

FIG. 19 is a view showing the cases in which the film is transparent to the illumination wavelength. If a very thin film or film with excellent wettability is on the top surface, the film conforming to the surface shape of under-layer is formed (FIG. 19A). In this case, the surface roughness of the top surface and the surface roughness of the under-layer are almost identical. On the other hand, if the film thickness is large, or the film with less wettability is on the top layer, the surface roughness is uncorrelated with the surface state of the substratum, whereby the surface roughness of the substratum is different between the top surface and the under-layer, as shown in FIG. 19B. According to [non-patent documents 4, 5 and 6], the value of $Q^{topo}$ is changed because of these differences, and in computing the light scattering of the film having transparent surface with the substrate by simulation, it is required to consider the film thickness or film materials.

Figure 20:
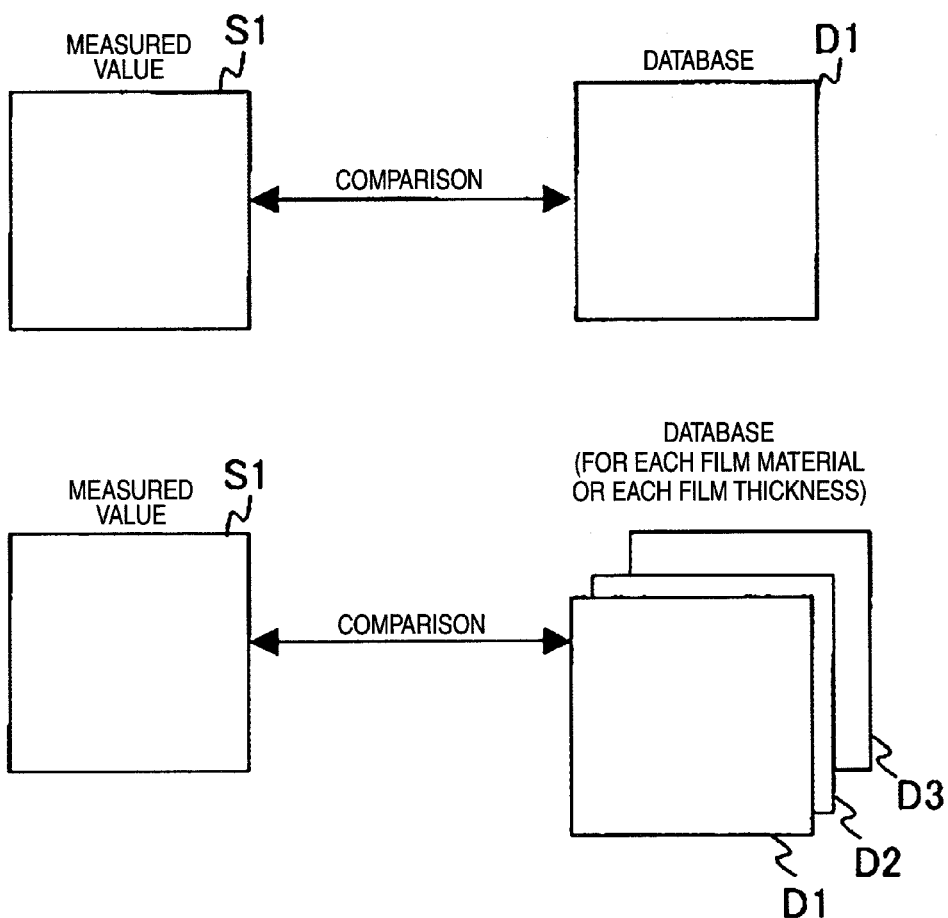
FIG. 20 is a view showing the comparison between the measured signal and the database.

FIG. 20 is a view showing a scheme for improving the computation efficiency in making the comparison with the database. If the information on the film materials or film thickness can be acquired before inspection, the search space can be reduced, and the evaluation for the degree of coincidence of vectors can be made faster. The film materials or film thickness may be inputted by the user who measures the substrate, or an ellipsometer may be mounted on a measurement sample alignment portion of the inspecting apparatus, for example, to measure the (optical constant of) film specifies or film thickness in parallel with the alignment. In this case, the computation efficiency can be improved without having any influence on the total inspection time of the substrate. If the approximate value of the film thickness is known, even though the accurate value is unknown, the search range can be reduced, whereby the computation efficiency is improved by inputting the approximate value. Also, using these information, there is less risk of estimating the different substrate indicating the similar scattering intensity distribution, even if the film materials or film thickness and the surface roughness are different, whereby the higher estimation precision can be expected.

A summary of the above described contents is represented in FIG. 21. A process 40 involves a computation algorithm for estimating the film materials, film thickness and surface state. The input values include the signal value of each detector, film materials, film thickness, and data on the surface roughness of the under-layer in the transparent film, in which the film materials, film thickness, and data on the surface roughness of the under-layer are used, only if available. The process 40 includes comparing the inputted signal value of each detector with the database, and estimating the surface roughness, film materials and film thickness. In the comparison with the database, if the distance between vectors is larger (in a sparse state in which there is no data closer to light scattering of the inspection object substrate in the database), the surface state of inspection object substrate may be estimated by a method of linear interpolation, using some vectors in the neighborhood.

Though the present invention has been specifically described above based on the embodiment of the invention achieved by the present inventor, the invention is not limited to the above embodiment, but needless to say, may be changed in various ways without departing from the spirit or scope of the invention. Also, though the inspecting apparatus for detecting the surface defect of the wafer has been exemplified in the above embodiment, the application object of the invention is not limited to this, and the techniques of the invention can be applied to the surface inspection of various kinds of substrate, such as the disk surface inspection of a hard disk or the like, a glass substrate inspection of liquid crystal or the like, photo mask surface inspection, in addition to the semiconductor substrate inspection.

With the invention, it is possible to provide an inspecting method and an inspecting apparatus for detecting the microroughness of the substrate surface at high sensitivity and high speed.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. An inspecting method for inspecting a substrate surface, characterized by including:
   a first step of illuminating a light to the substrate surface having a film;
   a second step of detecting a scattered light or reflected light from a plurality of positions of the substrate surface and obtaining a plurality of electrical signals;
   a third step of comparing the plurality of electrical signals and a database which indicates a relationship between the electrical signals and surface roughness; and
   a fourth step of calculating a surface roughness value based on the result of comparing of the third step; and
   wherein the relationship between electrical signals and surface roughness stored in the data base is a relationship based on frequency components of surface roughness corresponding to light diffraction of the light illuminated on the substrate surface.

2. The inspecting method according to claim 1, wherein the database is obtained beforehand by measurement or simulation of another substrate for which surface roughness is known.

3. The inspecting method according to claim 1, characterized in that the third step includes comparing the plurality of electrical signals and a database which indicates a relationship between the electrical signals and film thickness;
   characterized in that the fourth step includes calculating a film thickness based on the result of comparing of the third step.

4. The inspecting method according to claim 1, characterized in that the third step includes comparing the plurality of electrical signals and a database which indicates a relationship between the electrical signals and film materials;
   characterized in that the fourth step includes determining a film material based on the result of comparing of the third step.

5. The inspecting method according to claim 1, wherein the database indicates a relationship between the electrical signals of a respective detector and surface roughness.

6. The inspecting apparatus according to claim 1, characterized in that the comparator includes a comparing device which compares the plurality of electrical signals and a database which indicates a relationship between the electrical signals and film thickness;
   characterized in that the calculator calculates a film thickness based on the result of comparing of the comparing device.

7. An inspecting apparatus for inspecting a substrate surface, characterized by including:
   an illuminator which illuminates a light to the substrate surface having a film;
   at least one detector which detects a scattered light or reflected light from a plurality of positions of the substrate surface for obtaining a plurality of electrical signals;
   a comparator which compares the plurality of electrical signals and a database which indicates a relationship between the electrical signals and surface roughness; and
   a calculator which calculates a surface roughness value based on the result of comparing of the comparator,
   wherein the relationship between electrical signals and surface roughness stored in the data base is a relationship based on frequency components of surface roughness corresponding to light diffraction of the light illuminated on the substrate surface.

8. The inspecting apparatus according to claim 7, wherein the database is obtained beforehand by measurement or simulation of another substrate for which surface roughness is known.

9. The inspecting apparatus according to claim 7, characterized in that the comparator includes a comparing device which compares the plurality of electrical signals and a database which indicates a relationship between the electrical signals and film materials;
   characterized in that the calculator determines a film material based on the result of comparing of the comparing device.

10. The inspecting apparatus according to claim 7, wherein the database indicates a relationship between the electrical signals of a respective detector and surface roughness.

* * * * *